United States Patent
Ellies et al.

(10) Patent No.: US 12,195,461 B2
(45) Date of Patent: *Jan. 14, 2025

(54) PYRROLO-DIPYRIDINE COMPOUNDS

(71) Applicant: OssiFi Therapeutics LLC, Overland Park, KS (US)

(72) Inventors: Debra Ellies, Parkville, MO (US); F. Scott Kimball, Olathe, KS (US); Robert N. Young, Vancouver (CA)

(73) Assignee: OssiFi Therapeutics LLC, Overland Park, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/179,818

(22) Filed: Mar. 7, 2023

(65) Prior Publication Data

US 2023/0203036 A1 Jun. 29, 2023

Related U.S. Application Data

(60) Continuation of application No. 17/186,796, filed on Feb. 26, 2021, now Pat. No. 11,655,250, which is a division of application No. 16/539,915, filed on Aug. 13, 2019, now Pat. No. 10,947,236.

(60) Provisional application No. 62/718,612, filed on Aug. 14, 2018.

(51) Int. Cl.
| C07D 471/14 | (2006.01) |
| A61K 31/4375 | (2006.01) |
| A61L 27/28 | (2006.01) |
| A61L 27/36 | (2006.01) |
| A61L 27/40 | (2006.01) |
| A61L 27/54 | (2006.01) |
| A61P 19/10 | (2006.01) |

(52) U.S. Cl.
CPC ........ C07D 471/14 (2013.01); A61K 31/4375 (2013.01); A61L 27/28 (2013.01); A61L 27/365 (2013.01); A61L 27/40 (2013.01); A61L 27/54 (2013.01); A61P 19/10 (2018.01)

(58) Field of Classification Search
CPC .................................................. C07D 471/14
USPC ....................................................... 514/279
See application file for complete search history.

(56) References Cited

U.S. PATENT DOCUMENTS

| 2,688,022 A | 8/1954 | Burtner |
| 2,767,179 A | 10/1956 | Cavallito et al. |
| 2,800,474 A | 7/1957 | Voegtli |
| 5,298,852 A | 3/1994 | Meyer |
| 5,324,819 A | 6/1994 | Oppermann et al. |
| 5,344,654 A | 9/1994 | Rueger et al. |
| 5,468,845 A | 11/1995 | Oppermann et al. |
| 5,494,928 A | 2/1996 | Bos |
| 5,656,593 A | 8/1997 | Kuberasampath et al. |
| 5,939,039 A | 8/1999 | Sapieszko et al. |
| 6,190,880 B1 | 2/2001 | Israel et al. |
| 6,426,332 B1 | 7/2002 | Rueger et al. |
| 6,627,637 B2 | 9/2003 | Ritzeler et al. |
| 6,949,251 B2 | 9/2005 | Dalal et al. |
| 7,189,263 B2 | 3/2007 | Erbe et al. |
| 7,812,018 B2 | 10/2010 | Hepperle et al. |
| 8,119,655 B2 | 2/2012 | Dong et al. |
| 8,119,665 B2 | 2/2012 | Luke et al. |
| 8,338,448 B2 | 12/2012 | Clark et al. |
| 9,314,468 B2 | 4/2016 | Clark et al. |
| 9,540,365 B2 | 1/2017 | Ellies et al. |
| 10,501,457 B2 | 12/2019 | Ellies et al. |
| 10,947,236 B2 * | 3/2021 | Ellies ................. A61K 31/5375 |
| 11,267,814 B2 | 3/2022 | Ellies et al. |
| 11,655,250 B2 * | 5/2023 | Ellies ................. A61K 31/5375 |
| | | 546/82 |

(Continued)

FOREIGN PATENT DOCUMENTS

| CN | 101945867 A | 1/2011 |
| CN | 102796124 A | 11/2012 |

(Continued)

OTHER PUBLICATIONS

Banker and Rhodes, ed., "Modern Pharmaceutics," Third Edition, Revised and Expanded, Marcel Dekker, Inc., pp. 451 and 596 (1996).
CAPLUS, English Abstract, DN 155;674252, Francik Renata et al. 2011.
CAS Registry 475632-16-7, published on Dec. 11, 2002, 1 page.
CAS Registry No. 1026011-30-2, entered STN on Jun. 6, 2008, 1 page.
CAS Registry No. 1028272-52-7, entered STN on Jun. 15, 2018, 1 page.

(Continued)

*Primary Examiner* — Niloofar Rahmani
(74) *Attorney, Agent, or Firm* — Mintz Levin Cohn Ferris Glovsky and Popeo, P.C.

(57) ABSTRACT

In one aspect, the invention provides compounds of Formula I Formula Ia, Formula Ib, Formula Ic, and Formula Id and salts, hydrates and isomers thereof. In another aspect, the invention provides a method of promoting bone formation in a subject in need thereof by administering to the subject a therapeutically effective amount of a compound of Formula I, Formula Ia, Formula Ib, Formula Ic, or Formula Id. The present invention also provides orthopedic and periodontal devices, as well as methods for the treatment of renal disease, diabetes bone loss, and cancer, using a compound of Formula I, Formula Ia, Formula Ib, Formula Ic, or Formula Id.

23 Claims, 1 Drawing Sheet (I)

(56) References Cited

U.S. PATENT DOCUMENTS

| | | |
|---|---|---|
| 2002/0169122 A1 | 11/2002 | Majumdar et al. |
| 2002/0187104 A1 | 12/2002 | Li et al. |
| 2005/0085554 A1 | 4/2005 | Hamann et al. |
| 2006/0177475 A1 | 8/2006 | Rueger et al. |
| 2006/0178752 A1 | 8/2006 | Yaccarino et al. |
| 2006/0188542 A1 | 8/2006 | Bobyn et al. |
| 2006/0188544 A1 | 8/2006 | Saito |
| 2006/0204542 A1 | 9/2006 | Zhang et al. |
| 2006/0252724 A1 | 11/2006 | Lyons et al. |
| 2007/0054151 A1 | 3/2007 | Iwakuma et al. |
| 2007/0060606 A1 | 3/2007 | Robertson et al. |
| 2007/0172479 A1 | 7/2007 | Warne et al. |
| 2007/0191851 A1 | 8/2007 | Ashammakhi |
| 2010/0063085 A1 | 3/2010 | Cohen |
| 2010/0074939 A1 | 3/2010 | Ellies et al. |
| 2010/0173931 A1 | 7/2010 | Ellies et al. |
| 2012/0208809 A1 | 8/2012 | Babin et al. |
| 2012/0302755 A1 | 11/2012 | Szardenings et al. |
| 2013/0028958 A1 | 1/2013 | Rommelspacher |
| 2013/0131070 A1 | 5/2013 | Buolamwini |
| 2013/0315965 A1 | 11/2013 | Ellies et al. |
| 2016/0326162 A1 | 11/2016 | Lin et al. |
| 2017/0298059 A1 | 10/2017 | Ellies et al. |
| 2018/0127427 A1 | 5/2018 | Haas et al. |
| 2020/0054645 A1 | 2/2020 | Ellies et al. |
| 2020/0055853 A1 | 2/2020 | Ellies et al. |
| 2020/0172538 A1 | 6/2020 | Ellies et al. |
| 2022/0024922 A1 | 1/2022 | Ellies et al. |

FOREIGN PATENT DOCUMENTS

| | | |
|---|---|---|
| CN | 105120863 A | 12/2015 |
| DE | 4436190 | 4/1996 |
| EP | 0548553 | 6/1993 |
| EP | 0705831 | 4/1996 |
| EP | 0799829 | 10/1997 |
| EP | 0815110 | 1/1998 |
| EP | 1134221 | 9/2001 |
| EP | 1209158 | 5/2002 |
| FR | 2003999 | 11/1969 |
| GB | 1268772 A | 3/1972 |
| JP | 2005-530811 A | 10/2005 |
| JP | 2011-505379 A | 2/2011 |
| JP | 2016-519082 A | 5/2013 |
| JP | 2015-520152 A | 7/2015 |
| WO | WO-1994/006416 | 3/1994 |
| WO | WO-2000/002878 | 1/2000 |
| WO | WO-00/53180 A1 | 9/2000 |
| WO | WO-03/099814 | 12/2003 |
| WO | WO-2007/091707 | 8/2007 |
| WO | WO-2009/029625 | 3/2009 |
| WO | WO-2009/073620 | 6/2009 |
| WO | WO-2009/121063 | 10/2009 |
| WO | WO-2010/015636 | 2/2010 |
| WO | WO-2010/123583 | 10/2010 |
| WO | WO-2011/079841 | 7/2011 |
| WO | WO-2011/133795 | 10/2011 |
| WO | WO-2011/161256 | 12/2011 |
| WO | WO-2012/024433 | 2/2012 |
| WO | WO-2014/153203 | 9/2014 |
| WO | WO-2018/024643 A1 | 2/2018 |
| WO | 2020037004 A1 | 2/2020 |

OTHER PUBLICATIONS

Cuny et al., "Structure-activity relationship study of beta-carboline derivatives as haspin kinase inhibitors," Bioorganic Medicinal Chemistry Letters, vol. 22, Issue 5, pp. 2015-2019 (2012).

Dai et al., "The IκB Kinase (IKK) Inhibitor, NEMO-binding Domain Peptide, Blocks Osteoclastogenesis and Bone Erosion in Inflammatory Arthritis," The Journal of Biochemical Chemistry, 279(36), pp. 37219-37222 (2004).

Dhandayuthapani et al., "Polymeric Scaffolds in Tissue Engineering Application: A Review," International Journal of Polymer Science, vol. 2011, Article ID 290602, 19 pages (2011).

Ellies et al., "Bone Density Ligand, Sclerostin, Directly Interacts with LRP5 but Not LRP5$^{G171v}$ to Modulate Wnt Acitivity," Journal of Bone and Mineral Res., vol. 21(11), pp. 1738-1749 (2006).

Francik et al., "Antioxidant activity of ß-carboline derivatives," Acta Poloniae Pharmaceutica, 68(2), pp. 185-189 (2011).

Galarreta et al., "The use of natural product scaffolds as leads in the search for trypanothione reductase inhibitors," Bioorganic & Medicinal Chemistry, vol. 16, Issue 14, pp. 6689-6695 (2008).

Guan et al., "Design of ß-carboline Derivatives as DNA-targeting antitumor agents," European Journal of Medicinal Chemistry, 41, pp. 1167-1179 (2006).

Youssef, "Alkaloids of the flowers of Hippeastrum vittatum," J. Nat. Prod., 64(6):839-841 (Jun. 2001).

Ishida et al., "Antitumor Agents 201.1 Cytotoxicity of Harmine and ß-Carboline Analogs," Bioorganic & Medicinal Chemistry Letters, 9, pp. 3319-3324 (1999).

Jeffcoat, "Safety of oral bisphosphonates: controlled studies on alveolar bone," Journal of Oral and Maxillofacial Implants, vol. 21, pp. 349-353 (2006).

Kelly et al., "Maxonine: Structure correction and synthesis," Tetrahedron Letters, 34(39), pp. 6173-6176 (Sep. 24, 1993).

Koretskaya et al., "Synthesis of harmine derivatives," Zhurnal Obshchei Khimii, vol. 27, pp. 542-545 (1957) (English translation "Synthesis of harmine derivatives," The Journal of General Chemistry of the U.S.S.R., Feb. 1957, vol. 27 (2), pp. 611-614).

Kular et al., "An overview of the regulation of bone remodeling at the cellular level," Clinical Biochemistry, vol. 45, pp. 863-873 (2012).

Wolff, ed., "Burger's Medicinal Chemistry and Drug Discovery," Fifth Edition, vol. I: Principles and Practice, Immunopharmaceutics, Inc., pp. 975-977 (1995).

Li et al., "Sclerostin Antibody Treatment Increases Bone Formation, Bone Mass, and Bone Strength in a Rat Model of Postmenopausal Osteoporosis," J. Bone Miner Res., vol. 24(4), pp. 578-588 (2009).

Zhang et al., "Design and pharmacology of a highly specific dual FMS and KIT kinase inhibitor," PNAS, 110(14), pp. 5689-5694 (Apr. 2, 2013).

Obach, "Prediction of human clearance of twenty-nine drugs from hepatic microsomal intrinsic clearance data: An examination of in vitro half-life approach and nonspecific binding to microsomes," Drug Metab. Dispos., 27(11), pp. 1350-1359 (1999).

Zhelyazkov et al., "Synthesis from harmine," Farmatsiya (Sofia, Bulgaria) 7(1), pp. 29-33 (1957).

Schumacher et al., "Synthesis of Didemnolines A-D, N9-Substituted ß-Carboline Alkaloids from Marine Ascidian *Didemnum* sp.," Tetrahedron, vol. 55, Issue 4, pp. 935-942 (Jan. 22, 1999).

Schumacher and Davidson, "Didemnolines A-D, New N9-Substituted ß-Carbolines from the Marine Ascidian *Didemnum* sp," Tetrahedron 51(37), pp. 10125-10130 (1995).

Vaccaro, "The role of the osteoconductive scaffold in synthetic bone graft," Orthopedics, vol. 25(5 Suppl.), pp. s571-s578 (May 2002).

Vrijens et al. "Identification of small molecule activators of BMP signaling," PLoS One, 8(3), e59045, pp. 1-10 (2013).

Wan et al., "Parathyroid hormone signaling through low-density lipoprotein-related protein 6," Genes Dev., 22(21), pp. 2968-2979 (2008).

Wang et al., "A high-throughput chemical screen reveals that harmine-mediated inhibition of DYRK1A increases human pancreatic beta cell replication," Author manuscript, published in final edited form as: Nat Med., 21(4), pp. 383-388 (2015).

Williams et al., "Medical Progress—Periodontal Disease," New England Journal of Medicine, vol. 322(6), pp. 373-382 (Feb. 1990).

Yaffe et al., "Local Delivery of an Amino Bisphosphonate Prevents the Resorptive Phase of Alveolar Bone Following Mucoperiosteal Flap Surgery in Rats," Journal of Periodontology, vol. 68, pp. 884-889 (1997).

International Search Report and Written Opinion from PCT Application U2014/029582, Sep. 18, 2014 (12 pages).

International Search Report and Written Opinion for International Patent Application No. PCT/US2019/046415, mailed Nov. 15, 2019 (22 pages).

(56) References Cited

OTHER PUBLICATIONS

Japan Notice of Reasons for Rejection from JP Application No. 2021-507505 mailed Jun. 6, 2023.
Smith et al., (Feb. 25, 2008) "(Dimethoxy- and Dihalopyridyl)boronic Acids and Highly Functionalized Heteroarylpyridines by Suzuki Cross-Coupling Reactions", European Journal of Organic Chemistry, 2008 (8):1458-1463.

* cited by examiner

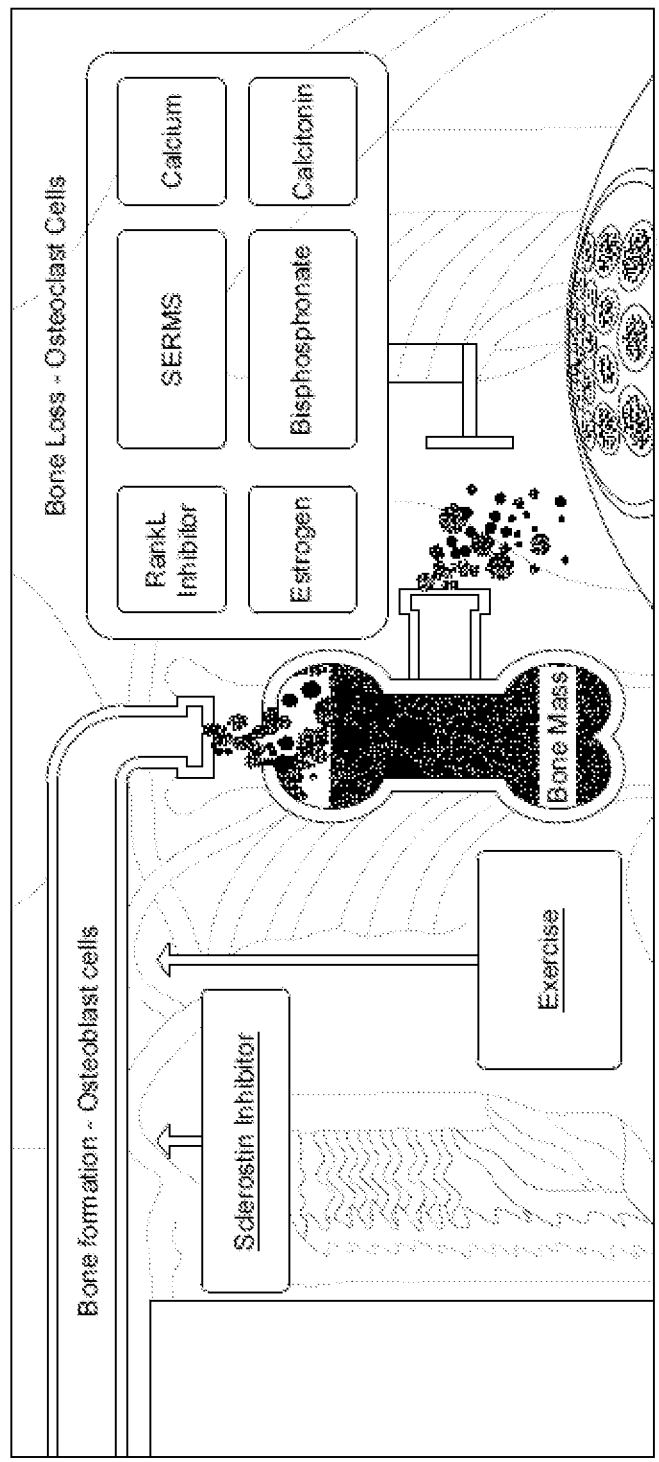

PYRROLO-DIPYRIDINE COMPOUNDS

CROSS-REFERENCES TO RELATED APPLICATIONS

This application is a continuation of U.S. patent application Ser. No. 17/186,796, filed Feb. 26, 2021, which is a divisional of U.S. application Ser. No. 16/539,915 filed Aug. 13, 2019, which claims the benefit of priority under 35 U.S.C § 119(e) to U.S. Provisional Application Ser. No. 62/718,612 filed Aug. 14, 2018, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Bone homeostasis involves the counterbalancing processes of bone formation and bone resorption. Increased bone resorption and loss of bone homeostasis is associated with a number of diseases and disorders, such as osteoporosis and Paget's disease. All FDA approved therapeutics for treating low bone density, except Teriparatide, do so by stopping bone resorption, hence antiresoptives. Antiresorptives act on the osteoclast cell by stopping them from resorbing the bone.

It is well known in the art that bone can be formed by two processes; one of which is mediated though a chondrocyte cartilage intermediate, (endochondral) and the other is a direct process that stimulates the osteoblast cells (intramembranous). The endochondral process involves chondrocytes/cartilage cells which die and leave a void space which become occupied by osteoblast cells that calcified on the surface of the chondrocyte cartilage calcification. During the resorption process the osteoclasts resorb this cartilage calcification leaving a clean non-cartilage bone mineral behind. The endochondral process is present during the rudimentary formation and growth of long bones, and during the cartilage callus process of bone fractures. Endochondral process begins when mesenchymal stem cells differentiate into chondrocytes creating cartilage. Whereas the intramembranous process occurs during new bone growth stage of bone fractures and formation of bones of the head. Intramembranous process occurs when mesenchymal stem cells differentiate into an osteoblast cell. Unlike cartilage, which is an elastic tissue, bone is hard and rigid. Two very different cellular processes (osteoblasts vs chondrocytes) involving different molecular (WNT vs BMP) and cellular mechanisms (osteoblasts vs chondrocytes).

It is well understood that osteoblast cells are responsible for secreting the bone mineral that causes increases in bone density. To date, only teriparatide was known to stimulate the osteoblast cell to increase mineral deposit, albeit indirectly through the Wnt pathway.

It is desirable to cause osteoblast mineral deposition (bone formation) for treatment of a wide variety of disparate disorders in mammals including simple aging, bone degeneration and osteoporosis, fracture healing, osteogenesis imperfecta, HPP, fusion of two bones or arthrodesis across a joint, any low bone density disorder, etc., as well as for successful installation of various medical orthopedic and periodontal implants such as screws, rods, titanium cage for spinal fusion, hip joints, knee joint, ankle joints, shoulder joints, dental implants, bone grafts, plates and rods, etc.

The use of antiresorptives such as, but not limited to; Cathepsin K inhibitors, Rank Ligand inhibitor, Denosumab, Prolia, an osteoprotegerin (OPG) inhibitor, alendronate, selective estrogen receptor modulators (SERMs), bisphosphonates, and the like for treating a subject with low bone density conditions has resulted, at least in part, with a very small initial increased bone mineral deposition of less than 6% in the first year followed by smaller gains in subsequent years. The overall gain in bone density from an antiresorptive therapy (stopping bone loss) has been reported at 9.4% over three years. Such treatable conditions may include osteopenia, osteoporosis, arthritis, tumor metastases, osteogenesis imperfecta, Paget's disease, secondary low bone density disorders/diseases and other metabolic bone disorders.

The use of Parathyroid hormone and analogs, Prostaglandin agonists, PDGE2, PDGE, Forteo, osteoprotegerin (OPG) inhibitor, teriparatide, BMP2, BMP7, BMP4, EP4 agonist and the like may be used for causing a desirable increase bone mineral in a subject with low bone density conditions. Such conditions may include osteopenia, osteoporosis, arthritis, tumor metastases, osteogenesis imperfecta, Paget's disease, secondary low bone density disorders, bone fusion, spinal fusion, arthrodesis and other metabolic bone disorders. However, the use of BMP agonists for treating systemic disease has not been pursued past an FDA Phase I Clinical Trial.

Additionally, it is known in the art the use of PTH, TGFβ binding proteins and like for increasing bone mineralization to treat conditions which may be characterized in part by increased fracture risk, such as osteopenia, degenerative disk disease, bone fractures, osteoporosis, arthritis, tumor metastases, osteogenesis imperfecta, Paget's disease, and other metabolic bone disorders Demineralized bone matrix is also known to be able to be partially conducive to small amount of new bone growth, due the endogenous growth factors (TGFβ binding proteins (BMPs)) surviving the sterilization procedure of the cadaver bone. However, demineralized bone matrix is generally sourced from donor cadaver banks and carries certain risks such as disease transmission or bacterial contamination. Other versions of demineralized bone matrix are more heavily processed and carry less disease risk. A current unmet medical need using current approved therapies in the field of non-union fractures is the desire to improve the poor healing observed in long bone large defects consisting of large voids between bone fracture ends. The use of demineralized bone or similar osteoconductive material, which is known in the art, has not resulted in the desired effects of fusing long bones.

Thus, there remains a need in the art for new methods of treating bone disorders, bone fractures and related issues. The present invention meets these and other needs.

BRIEF SUMMARY OF THE INVENTION

In one aspect, the present invention provides compounds and compositions, as well as methods of using such compounds and compositions. In a first embodiment, the present invention provides compounds of Formula I:

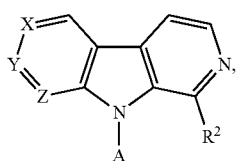

or a salt, hydrate, prodrug, or isomer thereof, wherein
X is selected from $CR^{3b}$ and N, wherein N is optionally oxidized to the corresponding N-oxide;
Y is selected from $CR^{3c}$ and N, wherein N is optionally oxidized to the corresponding N-oxide;
Z is selected from $CR^{3d}$ and N, wherein N is optionally oxidized to the corresponding N-oxide,
provided that at least one of X, Y, and Z is N or the corresponding N-oxide;
A is

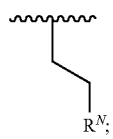

$R^N$ is selected from the group consisting of heterocyclyl and heteroaryl, wherein
the heterocyclyl moiety is selected from monocyclic, fused bicyclic, and bridged cyclic, the monocyclic heterocyclyl comprising from 4 to 7 ring members, the fused bicyclic and bridged bicyclic heterocyclyl comprising from 7 to 10 ring members, each heterocyclyl moiety having from 1 to 3 heteroatoms as ring members selected from N, O, and S, wherein each heterocyclyl moiety comprises at least one nitrogen atom as a ring member and is optionally substituted with from 1 to 3 $R^6$ moieties,
the heteroaryl moiety comprises from 5 to 10 ring members, wherein at least one ring member is a nitrogen atom and is optionally substituted with from 1 to 3 $R^6$ moieties,
each $R^2$, $R^{3b}$, $R^{3c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkyl-OH, —O—$C_{1-6}$ alkyl-OH, $C_{3-6}$ cycloalkyl-$C_{1-4}$alkoxy, and —OH; and
$R^6$ is selected from the group consisting of —OH, $C_{1-3}$ alkyl, $C_{1-3}$ alkyl-OH, —O—$C_{1-3}$ alkyl, $C_{3-4}$ heteroalkyl, $C_{1-3}$ haloalkyl, —O—$C_{1-3}$ haloalkyl, halogen, and oxo.

In a second embodiment, the present invention provides a method of promoting bone formation and fusion in a subject in need thereof. The method includes administering to the subject a therapeutically effective amount of a compound of Formula I, Formula Ia, Formula Ib, Formula Ic, or Formula Id as described herein, thereby promoting bone formation in the subject. Bone formation can be systemic or local. For local bone formation, in some embodiments the compound may be administered with an osteoconductive agent, e.g., an osteoconductive matrix.

In a third embodiment, the present invention provides a method of treating renal damage. The method includes administering to a subject in need thereof, a therapeutically effective amount of a compound of Formula I, Formula Ia, Formula Ib, Formula Ic, or Formula Id.

In a fourth embodiment, the present invention provides a method of treating diabetes. The method includes administering to a subject in need thereof, a therapeutically effective amount of a compound of Formula I, Formula Ia, Formula Ib, Formula Ic, or Formula Id.

In a fifth embodiment, the present invention provides a method of treating cancer. The method includes administering to a subject in need thereof, a therapeutically effective amount of a compound of Formula I, Formula Ia, Formula Ib, Formula Ic, or Formula Id.

In a sixth embodiment, the present invention provides a medical device, e.g., an orthopedic or periodontal medical device. The device includes a structural support, wherein an implantable portion of the structural support is adapted to be permanently implanted within a subject. The implantable portion is attached to a bone, and the structural support bears at least a partial external coating including a compound of Formula I, Formula Ia, Formula Ib, Formula Ic, or Formula Id.

In a seventh embodiment, the present invention provides compounds or compositions as described herein (e.g., a compound or composition of Formula I, Formula Ia, or Formula Ib, Formula Ic, or Formula Id) for use in the preparation of a medicament for the treatment of a disease or condition as described herein. In some embodiments, the disease or condition is injured bone, bone fracture, weakened bone, osteogenesis imperfecta, hypophosphatasia (HPP), osteopenia, osteoporosis, arthrodesis or a condition characterized by low bone mass or density. Also contemplated herein is the use of the compounds or compositions described herein in periodontal implants or medical orthopedic implants. Orthopedic implants include screws, rods, as well as titanium cages for us in, for example, spinal fusion.

In an eighth embodiment, the present invention provides a orthobiologic, e.g., a bone formation inducer for surgical implantation with or without a bone graft device. The device includes a structural support, wherein an implantable portion of the structural support is adapted to be permanently implanted within a subject. The implantable portion is attached to a bone, and the structural support bears at least a partial external coating including a compound of Formula I, Formula Ia, Formula Ib, Formula Ic, or Formula Id.

In a ninth embodiment, the present invention provides a method of treating bone loss. The method includes administering to a subject in need thereof, a therapeutically effective amount of a compound of Formula I, Formula Ia, Formula Ib, Formula Ic, or Formula Id in series or in combination with an antiresorptive agent.

BRIEF DESCRIPTION OF THE DRAWINGS

FIG. 1: Bone mass homeostasis is regulated by the coupled process of bone formation (increasing the amount of bone mineral deposit) and the process of bone resorption (decreasing the amount of bone mineral deposit). Bone formation can be positively promoted by activities and agents that act on the osteoblast bone-forming cell, such as exercise, and indirectly by PTH (teriparatide), or by sclerostin inhibitors such as the compounds of the present invention. Bone resorption can be inhibited by antiresorptive agents such as RankL inhibitor, selective estrogen receptor modulator (SERM), calcium, estrogen, alendronate, fosamax, denosumab, prolia, cathepsin K modulators, bisphosphonates, calcitonin, and other agents acting to stop the activity of the osteoclast cell.

DETAILED DESCRIPTION OF THE INVENTION

I. Introduction

Bone mass homeostasis and bone remodeling involve the counterbalancing processes of bone formation (osteoblast cell depositing mineral, an anabolic process) and bone resorption (osteoclast cell resorbing mineral, bone loss, a catabolic process). These two processes are coupled in a healthy bone. See, FIG. 1. In bone formation, osteoblasts synthesize bone matrix and regulate mineralization, and then terminally differentiate into osteocytes or bone lining cells. In bone resorption, a different cell type—osteoclasts—remove mineralized bone matrix and break up the organic bone to release calcium in the serum. See, e.g., Kular et al., *Clinical Biochemistry* 45:863-873 (2012).

The osteoblasts (bone formation cells) and osteoclasts (bone resorption cells) are regulated by different mechanisms. Osteoclast cell differentiation is regulated or controlled by the osteoblast (Glass et al., *Dev Cell* 8:751-764 (2005)) or other hormones like PTH, calcitonin, or IL6. In contrast, osteoblast cell differentiation or activity is not regulated or controlled by osteoclast cells, but rather are controlled by different signals, like CPFA, hedgehog, WNT/LRP, and sclerostin. Bone formation can occur via endochondral ossificiation or intramembranous ossification (sclerostin). In intramembranous ossification, bone forms directly through the stimulation of osteoblast/osteocyte bone cells. In endochondral ossification, bone formation occurs by way of a cartilage template, which increases the amount of time that it takes bone to form. BMP signaling is implicated in endochondral ossification, whereas Wnt signaling has been shown to be involved in both endochondral and intramembranous ossification.

Under normal healthy conditions, bone remodeling (or bone homeostasis) involves the degradation of old bone (via osteoclast cells) and the repair or replacement of the old bone with new bone (via osteoblast cells). When this homeostasis is disrupted and bone resorption exceeds bone formation, i.e. diseased bone state, the results uncouple bone resorption from bone formation. Increased bone resorption leads to decreased bone mass (loss of trabecular bone) and greater bone fragility (less bone strength). A number of diseases and conditions are associated with increased bone resorption, including osteoporosis, osteogenesis imperfecta, Paget's disease of bone, metabolic bone disease, bone changes secondary to cancer, and other diseases characterized or associated with low bone density.

Diseases caused by increased bone resorption are associated with decreased bone mass and greater bone fragility and are frequently treated with antiresorptive agents such as bisphosphonates, denosumab, prolia, alendronate, cathepsin K modulators, RankL inhibitors, estrogens, cathepsin K inhibitors, and selective estrogen receptor modulators, to name but a few. These agents function by preventing or inhibiting osteoclast cell bone resorption, either directly or indirectly. See, FIG. 1. However, these agents do not promote the formation of new bone by the osteoblast cell (i.e., anabolic bone formation); in contrast, administration of one dose of an anabolic agent normally results in the an annual cumulative increase of >8% from baseline in bone formation in lumbar vertebra of humans). Administration of an antiresorptive does result in a modest increase in bone density the first year of <7% but thereafter the increase in bone density is <3.5% with an annual cumulative increase of <10%. Therefore, although a fragile osteoporotic bone that is treated with an antiresorptive agent will result in the fragile bone not getting more fragile, the fragile bone will not be stronger or have increased strength because the antiresorptive agent does not promote new bone growth by depositing more bone mineral to increase bone density. In contrast, an agent that promotes anabolic bone growth, for example, by stimulating the activity of osteoblasts, promotes the deposition of more bone matrix, or if proliferation were stimulated, the agent would result in more osteoblast cells, thus resulting in more bone cells to bridge a gap to fuse two bones. Thus, a fragile osteoporotic bone treated with an anabolic bone formation agent will allow the bone not to get more fragile, and also will allow the bone to have more strength due to increased bone formation.

With reference to FIG. 1, and without being bound to a particular theory, if one thinks of the bone as a bathtub, the drain is reminiscent of bone loss or resorption and the faucet reminiscent of the bone being added or bone formation. Both the faucet and drain are adding and removing at the same rate (coupled) until one ages or a disease strikes causing either the faucet to be turned down or the drain to be increased in size. Perturbations such as these result in an imbalance (uncoupling) of formation/resorption causing bone density to become lowered. For example, imagine a sponge that has an outer core and on the inside is made of fibers stretching from one end to the other. During bone resorption these fibers are removed, and if bone resorption is occurring at a rate faster than bone building or formation then these fibers would be few and the bone would become fragile. It would not take much strength to break a sponge with few inside fibers versus one with many inside fibers. Because the process of bone resorption is well understood, many of the marketed therapeutics stop bone resorption by acting on the osteoclast cells. These include antiresorptive agents such as Cathepsin K inhibitors, Rank Ligand inhibitor, Denosumab, Prolia, Fosamax, Evista, Premarin, osteoprotegerin (OPG) inhibitors, alendronate, selective estrogen receptor modulators (SERMs), bisphosphonates, and other agents acting to stop the activity of the osteoclast cell.

While still considering the analogy of the sponge, to increase bone strength, the number of fibers on the inside of the bone to increase bone strength. However, is not possible to increase bone strength by acting on the bone resorbing cell, the osteoclast. Thus, one needs to focus on the bone forming osteoblast cell. Unlike bone resorption, bone formation is not well understood and, until recently, only one systemic therapeutic (teriparatide) and one surgical implant (Infuse with BMP protein) has been marketed to promote bone formation. However, BMP product acts to increase chondrocytes and promote cartilage production. This process sometimes leads to the chondrocytes then being replaced by osteoblasts.

Intermittent teriparatide administration increases bone density systemically by activation of PKA which then phosphorylates LRP and activates the WNT pathway (Wan et al., *Genes Dev.* 22(21): 2968-2979 (2008)). This increase in bone density occurs along already laid down trabeculae within the bone matrix. The osteoblast cells lining the trabeculae secrete mineral unto the existing trabecular bone thus increasing the amount of mineral and density of the trabeculae.

When a bone void exists whereby a large segment of bone is removed causing non-union of the bone or a critical size defect. The bone is unable to heal itself across a large gap.

The addition of BMP to the site causes the pluripotent cells to differentiate into chondrocytes/cartilage and produce a cartilage callus. The ability of the gap to be filled by bone instead of cartilage would require osteoblast bone cells to undergo proliferation to fill the gap and then to deposit mineral to fill the void.

Without being bound to a particular theory, it is believed that compounds of the present invention are SOST (Sclerostin) and/or WISE antagonists that function by modulating the Wnt/LRP and/or BMP signaling pathways. SOST and WISE are proteins that are believed to modulate bone formation by either binding to the Wnt co-receptor LRP, thereby inhibiting the Wnt signaling pathway, or by binding to BMP and inhibiting BMP activity, via different amino acid sequences or domains. By neutralizing the inhibitory effects of SOST and/or WISE proteins on the Wnt pathway, the compounds and compositions of the present invention restore Wnt signaling and promote bone formation/growth. Thus, in one aspect, the present invention provides compounds, compositions, and methods for promoting bone formation in a subject. The bone formation can be systemic or local. The compounds and compositions of the present invention can be administered locally and/or systemically and optionally can be administered sequentially or in combination with one or more other therapeutic agents. In another aspect, the present invention provides implantable devices as structural scaffolds for allowing osteoblast/osteocytes to migrate into the scaffold and deposit bone mineral and also for delivering the compounds and compositions of the present invention, e.g., for promoting bone formation at the site of implantation. In another aspect, the compounds and compositions of the present invention can be used to treat renal damage, diabetes, bone loss, and cancer.

II. Definitions

As used herein, the term "pharmaceutically acceptable excipient" refers to a substance that aids the administration of an active agent to and absorption by a subject. Pharmaceutically acceptable excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the term "alkyl" refers to a straight or branched, saturated, aliphatic radical having the number of carbon atoms indicated. For example, $C_1$-$C_6$ alkyl (or $C_{1-6}$ alkyl) includes, but is not limited to, methyl, ethyl, propyl, butyl, pentyl, hexyl, iso-propyl, iso-butyl, sec-butyl, tert-butyl, etc.

Alkylene represents either straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain monosubstituted by $C_1$-$C_3$-alkyl (preferably methyl) or disubstituted on the same or different carbon atoms by $C_1$-$C_3$-alkyl (preferably methyl), the total number of carbon atoms being up to and including 7. One of skill in the art will appreciate that a single carbon of the alkylene can be divalent, such as in —$CH((CH_2)_nCH_3)$—, wherein n=0-5.

As used herein, the term "alkoxy" or "—O-alkyl" refers to alkyl with the inclusion of an oxygen atom, for example, methoxy, ethoxy, etc. "Haloalkoxy" is as defined for alkoxy where some or all of the hydrogen atoms are substituted with halogen atoms. For example, halo-substituted-alkoxy includes trifluoromethoxy, etc.

The term "hydroxyalkyl" or "alkyl-OH" refers to an alkyl group, as defined above, where at least one of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxy-methyl, hydroxy-ethyl (where the hydroxy is in the 1- or 2-position), hydroxy-propyl (where the hydroxy is in the 1-, 2- or 3-position), etc.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl or butynyl.

As used herein, the term "halogen" refers to fluorine, chlorine, bromine and iodine.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, etc. The term "perfluoro" defines a compound or radical which has at least two available hydrogens substituted with fluorine. For example, perfluoromethane refers to 1,1,1-trifluoromethyl, and perfluoromethoxy refers to 1,1,1-trifluoromethoxy.

As used herein, the term "heteroalkyl" refers to an alkyl group having from 1 to 3 heteroatoms such as N, O and S. Heteroalkyl groups have the indicated number of carbon atoms where at least one non-terminal carbon is replaced with a heteroatom. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. Heteroalkyl groups do not include peroxides (—O—O—) or other consecutively linked heteroatoms.

As used herein, the term "oxo" refers to a double bonded oxygen (=O).

As used herein, the term "cycloalkyl" refers to a saturated or partially unsaturated, monocyclic, fused bicyclic or bridged polycyclic ring assembly containing from 3 to 12 ring atoms, 3 to 8, 3 to 6, or the number of atoms indicated. For example, $C_{3-8}$ cycloalkyl includes cyclopropyl, cyclobutyl, cyclopentyl, cyclohexyl, and up to cyclooctyl. The cycloalkyl groups of the present invention are optionally substituted as defined below.

As used herein, the terms "heterocycle," "heterocycloalkyl," and "heterocyclyl" refer to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. The term heterocycle includes monocyclic, fused bicyclic, and bridged cyclic moieties. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl hexahydro-1H-furo[3,4-c]pyrrolyl and 1,4-dioxa-8-aza-spiro[4.5]dec-8-yl. The heterocycloalkyl groups of the present invention are optionally substituted as defined below.

Substituents for the cycloalkyl and heterocyclyl groups are varied and are independently selected from: -halogen, $C_{1-8}$alkyl, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —S(O)R', —S(O)$_2$R', —S(O)$_2$NR'R", perfluoro($C_1$-$C_4$)alkoxy, and perfluoro($C_1$-$C_4$)alkyl, in a number ranging from zero to the total number of open valences on the ring system; and where R', R" and R"' are independently selected from hydrogen, ($C_1$-$C_8$)alkyl and $C_{3-8}$ heteroalkyl, and phenyl.

As used herein, a group "linked via a carbon atom" refers to a linkage between a carbon atom of the referenced group and the rest of the molecule. A group "linked via a nitrogen atom" refers to a linkage between a nitrogen atom of the referenced group and the rest of the molecule. By way of example only, a heterocyclyl group linked via a carbon atom may be:

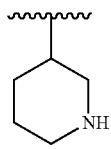

where the wavy line indicates the point of attachment to the rest of the molecule. By way of example only, a heterocyclyl group linked via a nitrogen atom may be:

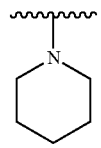

where the wavy line indicates the point of attachment to the rest of the molecule.

As used herein, where a referenced compound is an N-oxide, it comprises an N—O bond with three additional bonds to the nitrogen, i.e., an N-oxide refers to a group $R_3N^+$—$O^-$. By way of example only, N-oxides may include:

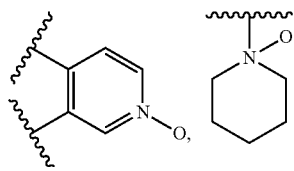

and the like.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals as described below.

Substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", alkylenedioxy, heteroaryl, —$C_{1-2}$ alkylene-heteroaryl, heterocyclyl, $C_{1-2}$alkylene-heterocyclyl, phenyl, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, ($C_1$-$C_8$)alkyl and $C_{3-8}$ heteroalkyl, and phenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene.

Examples of substituted phenyl groups include, but are not limited to 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic or heteroaryl ring.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl. Heteroaryl moieties can be optionally substituted, as defined below.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Substituents for the heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_5$)alkyl and $C_{3-8}$ heteroalkyl, and phenyl.

As used herein, the terms "ring members" and "ring vertices" are intended to have the same meaning. For example, a six membered ring has six ring vertices.

As used herein, the term "salt" refers to acid or base salts of the compounds used in the methods of the present invention. Illustrative examples of pharmaceutically acceptable salts are mineral acid (hydrochloric acid, hydrobromic acid, sulfuric acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly, acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "calcium salt" refers to salts containing calcium. Examples of calcium salts include, but are not limited to, calcium acetate, calcium aluminates, calcium aluminosilicate, calcium arsenate, calcium borate, calcium bromide, calcium carbide, calcium carbonate, calcium chlorate, calcium chloride, calcium citrate, calcium citrate malate, calcium cyanamide, calcium dihydrogen phosphate, calcium fluoride, calcium formate, calcium glubionate, calcium glucoheptonate, calcium gluconate, calcium glycerylphosphate, calcium hexaboride, calcium hydride, calcium hydroxide, calcium hypochlorite, calcium inosinate, calcium iodate, calcium iodide, calcium lactate, calcium lactate gluconate, calcium magnesium acetate, calcium malate, calcium nitrate, calcium nitride, calcium oxalate, calcium oxide, calcium pangamate, calcium peroxide, calcium phosphate, calcium phosphide, calcium propionate, calcium pyrophosphate, calcium silicate, calcium silicide, calcium sorbate, calcium stearate, calcium sulfate, calcium sulfide, calcium tartrate, calcium(I) chloride, dicalcium citrate, dicalcium phosphate, dodecacalcium heptaaluminate, tricalcium aluminate, tricalcium phosphate and triple superphosphate. One of skill in the art will appreciate that other calcium salts are useful in the present invention.

As used herein, the term "hydrate" refers to a compound that is complexed to at least one water molecule. The compounds of the present invention can be complexed with from 1 to 10 water molecules. The term "hydrate" also includes hemi-hydrates, where there are two compounds for every water molecules in the complex.

Certain compounds of the present invention possess asymmetric carbon atoms (optical centers) or double bonds; the racemates, diastereomers, geometric isomers and individual isomers are all intended to be encompassed within the scope of the present invention.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "site of injury or localized condition" refers to a specific location in the subject's body that is in need of treatment by the method of the present invention. For example, the injury can be a fracture and the localized condition can be a disease state (such as osteoporosis, etc.) that is limited to a particular location in the subject's body, such as a particular bone, joint, digit, hand, foot, limb, spine, head, torso, etc. In some embodiments, the site of injury or localized condition is a surgical implantation site.

As used herein, the term "promoting bone formation" refers to stimulating new bone formation, growing bone across a joint or gap, enhancing or hastening bone formation, and/or increasing bone density or bone mineral content. In some embodiments, a compound promotes bone formation if it increases the amount of bone in a sample by at least 3%, 4%, 5%, 6%, 7%, 8%, 9%, 10%, 11%, 12%, 13%, 14%, 15%, 16%, 17%, 18%, 19%, 20%, or more relative to a control sample (e.g., a sample that has not been contacted with the compound).

As used herein, the term "arthrodesis" refers to the artificial induction of joint ossification between two bones and/or across a joint, often via surgery. Arthrodesis can be accomplished via bone graft, metal implants or the use of synthetic bone substitutes, among others.

As used herein, the term "bone autograft" refers to the grafting of a subject's own bone.

As used herein, the term "bone allograft" refers to the grafting of bone from one person to another person.

As used herein, the term "antiresorptive drug" refers to drugs that slow or block the resorption of bone and/or that act on the osteoclast cell.

As used herein, the term "bone related disease characterized by low bone mass" refers to bone having a T-score less than −0.5. Other methods of determining low bone mass are known by one of skill in the art.

As used herein, the term "bone fracture" refers to bone that has been cracked, fractured, or broken in one or several locations along the bone. In some embodiments, the term "bone fracture" also includes a segment of the bond missing.

As used herein, the term "spinal fusion" refers to a surgical technique for combining or fusing two or more vertebrae.

As used herein, the term "structural support" refers to a segment of a device that can be implanted in a subject (implantable portion). The structural support can be prepared from a variety of different materials, including metals, ceramics, polymers and inorganic materials, such as described below. The structural support can be coated with a variety of materials that promote bone growth. In some embodiments, the entire device comprises an implantable structural support. For example, in some embodiments, an entire device as described herein can be implanted at a surgical site and the surgical site can be closed over the device.

As used herein, the term "external coating" refers to a coating of the structural support that can cover only a portion of the structural support (partial external coating) or cover the entire structural support. For example, the partial external coating can completely cover only the implantable portion of the structural support.

As used herein, the term "weakened bone," "low bone density," or "low bone mass" refers to bone that has a T score of less than −0.5 (less than 0.9 g/cm2).

As used herein, the term "demineralized bone" refers to bone from which the inorganic mineral have been removed. The remaining organic collagen material may contain the osteoinductive growth factors. These growth factors include bone morphogenetic proteins that induce cartilage which then ossify via endochondral ossification to generate new bone formation. Demineralized bone often comes in the form of "demineralized bone matrix (DBM)." DBM can be made by fresh frozen or freeze dried bulk bone allograft, or can be made from mild acid extraction of cadaveric bone that removes the mineral phase, leaving collagen, growth factors, and noncollagenous proteins that offer the intrinsic properties of osteoconduction. DBM can also be processed in a variety of ways, ultimately resulting in a powder that is mixed with a carrier to provide the optimum handling characteristics desired by a surgeon. DBM is clinically available in gels, pastes, putty, and fabrics that have been tailored to meet the needs of the surgical procedure. Some DBM are mixed with antibiotics prior to the surgical procedure.

As used herein, the term "renal damage" refers to the inability of the kidneys to excrete waste and to help maintain the electrolyte balance of the body. Renal damage is characterized by some of the following: high blood pressure, accumulation of urea and formation of uremic frost, accumulation of potassium in the blood, decrease in erythropoietin synthesis, increase in fluid volume, hyperphosphatemia, and metabolic acidosis, among others.

As used herein, the term "diabetes" refers to a condition primarily characterized by a body's inability to produce sufficient amounts of insulin, a hormone produced in the pancreas. When released in the blood steam, insulin induces cellular glucose uptake. As such, insufficient amounts of insulin result in elevated blood glucose levels in affected individuals. A person of skill in the art will recognize that the body's inability to produce sufficient amounts of insulin can be a characteristic of both Type 1 and Type 2 Diabetes.

As used herein, the term "osteoconductive matrix" refers to a material that can act as an osteoconductive substrate (i.e., permits bone growth) and has a scaffolding structure on which infiltrating cells can attach, proliferate, and participate in the process of producing osteoid, the organic phase of bone, culminating in osteoneogenesis, or new bone formation. The terms "matrix" and "scaffold" interchangeably refer to a structural component or substrate intrinsically having a 3 dimensional form upon which the specific cellular events involved in bone formation will occur. The osteoconductive matrix allows for the ingrowth of host capillaries, perivascular tissue and osteoprogenitor cells. In some embodiments, an osteoconductive matrix includes an "osteoinductive agent" for providing osteogenic potential. An osteoinductive agent, as used herein, is an agent that stimulates the host to multiply bone cells, thus producing more bone osteoid.

As used herein, the terms "treat," "treating," and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "RankL inhibitor" refers to compounds or agents that inhibit the activity of RankL. RankL (Receptor Activator for Nuclear Factor κ B Ligand), is important in bone metabolism by activating osteoclasts. RankL inhibitors include, but are not limited to, the human monoclonal antibody denosumab. One of skill in the art will appreciate that other RankL inhibitors are useful in the present invention.

As used herein, the term "parathyroid hormone" or "PTH" refers to compounds or agents that act on the PTH receptor to activate the pathway. PTH is important in bone metabolism by activating osteoblasts. PTH include, but are not limited to, Teriparatide, Forteo, and abaloparatide-SC. One of skill in the art will appreciate that other PTH are useful in the present invention.

As used herein, the term "combination therapy" is the use of the present invention in combination either together, or serially before or after the administration of compounds of this invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. In some embodiments, the compounds of the present invention are a particular enantiomer or diastereomer substantially free of other forms. The compounds of the present invention may also contain unnatural proportions of atomic isotopes at one or more of the atoms that constitute such compounds. For example, the compounds may be radiolabeled with radioactive or non-radioactive isotopes, such as for example deuterium ($^2H$), tritium ($^3H$), iodine-125 ($^{125}I$) or carbon-14 ($^{14}C$). All isotopic variations of the compounds of the present invention, whether radioactive or not, are intended to be encompassed within the scope of the present invention.

III. Compounds and Compositions

In some embodiments, the present invention provides a compound according to Formula I:

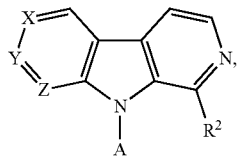

(I)

or a salt, hydrate, prodrug, or isomer thereof, wherein

X is selected from $CR^{3b}$ and N, wherein N is optionally oxidized to the corresponding N-oxide;

Y is selected from $CR^{3c}$ and N, wherein N is optionally oxidized to the corresponding N-oxide;

Z is selected from $CR^{3d}$ and N, wherein N is optionally oxidized to the corresponding N-oxide, provided that at least one of X, Y, and Z is N or the corresponding N-oxide;

A is

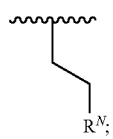

$R^N$ is selected from the group consisting of heterocyclyl and heteroaryl, wherein the heterocyclyl moiety is selected from monocyclic, fused bicyclic, and bridged cyclic, the monocyclic heterocyclyl comprising from 4 to 7 ring members, the fused bicyclic and bridged bicyclic heterocyclyl comprising from 7 to 10 ring members, each heterocyclyl moiety having from 1 to 3 heteroatoms as ring members selected from N, O, and S, wherein each heterocyclyl moiety comprises at least one nitrogen atom as a ring member and is optionally substituted with from 1 to 3 $R^6$ moieties, the heteroaryl moiety comprises from 5 to 10 ring members, wherein at least one ring member is a nitrogen atom and is optionally substituted with from 1 to 3 $R^6$ moieties, each $R^2$, $R^{3b}$, $R^{3c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkyl-OH, —O—$C_{1-6}$ alkyl-OH, $C_{3-6}$ cycloalkyl-$C_{1-4}$alkoxy, and —OH;

$R^6$ is selected from the group consisting of —OH, $C_{1-3}$ alkyl, $C_{1-3}$ alkyl-OH, —O—$C_{1-3}$ alkyl, $C_{3-4}$ heteroalkyl, $C_{1-3}$ haloalkyl, —O—$C_{1-3}$ haloalkyl, halogen, and oxo.

In some embodiments, the present invention provides a compound according to Formula Ia:

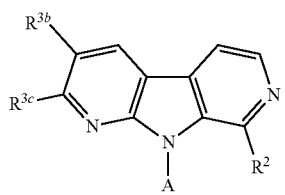

(Ia)

wherein each variable position is as defined in Formula I.

In some embodiments, the present invention provides a compound according to Formula Ib:

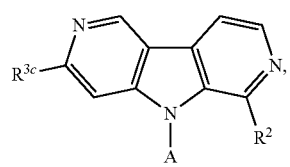

(Ib)

wherein each variable position is as defined in Formula I.

In some embodiments, the present invention provides a compound according to Formula Ic:

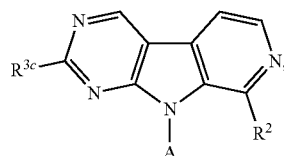

(Ic)

wherein each variable position is as defined in Formula I.

In some embodiments, the present invention provides a compound according to Formula Id:

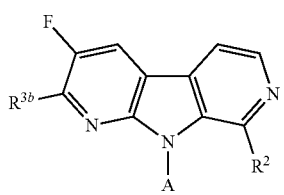

(Id)

wherein each variable position is as defined in Formula I.

In some embodiments, each $R^2$ in Formulas I, Ia, Ib, Ic, or Id is independently selected from the group consisting of halogen, $C_{1-6}$ alkyl, $C_{1-6}$ haloalkyl, and $C_{1-6}$ alkoxy. In some embodiments, $R^2$ in Formulas I, Ia, Ib, Ic, or Id is $C_{1-6}$ alkyl or $C_{1-6}$ haloalkyl. In some embodiments, $R^2$ in Formulas I, Ia, Ib, Ic, or Id is $CH_3$ or $CF_3$. In some embodiments, $R^2$ in Formulas I, Ia, Ib, Ic, or Id is $CF_3$.

In some embodiments, each $R^{3b}$, $R^{3c}$ and $R^{3d}$, when present in Formulas I, Ia, Ib, Ic, or Id is independently selected from the group consisting of H, halogen, $C_{1-6}$ alkyl, $C_{1-6}$ haloalkyl, $C_{1-6}$ alkoxy, $C_{1-6}$ haloalkoxy. In some embodiments, each $R^{3b}$, $R^{3c}$ and $R^{3d}$, when present in Formulas I, Ia, Ib, Ic, or Id is H, halogen, and $C_{1-6}$ alkoxy. In some embodiments, each $R^{3b}$, $R^{3c}$ and $R^{3d}$, when present in Formulas I, Ia, Ib, Ic, or Id is H, F, and methoxy. In some embodiments, at least one of $R^{3b}$, $R^{3c}$ and $R^{3d}$ when present in Formulas I, Ia, Ib, Ic, or Id is F. In some embodiments, at least one of $R^{3b}$, $R^{3c}$ and $R^{3d}$ when present in Formulas I, Ia, Ib, Ic, or Id is methoxy. In some embodiments, at least one of $R^{3b}$, $R^{3c}$ and $R^{3d}$ when present in Formulas I, Ia, Ib, Ic, or Id is F and at least one of $R^{3b}$, $R^{3c}$ and $R^{3d}$ is methoxy.

In some embodiments, $R^N$ of Formulas I, Ia, Ib, Ic, or Id is a heteroaryl. In some embodiments, the heteroaryl moiety comprises from 4 to 8 ring members, wherein at least one ring member is a nitrogen atom and is optionally substituted with from 1 to 3 $R^6$ moieties In some embodiments, $R^N$ of Formulas I, Ia, Ib, Ic, or Id is a monocyclic heterocyclyl.

In some embodiments, $R^N$ in Formulas I, Ia, Ib, Ic, or Id is

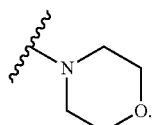

In some embodiments, $R^6$ in Formulas I, Ia, Ib, Ic, or Id is selected form the group consisting of —OH, $C_{1-3}$ alkyl, $C_{1-3}$ alkyl-OH, —O—$C_{1-3}$ alkyl, $C_{1-3}$ haloalkyl, —O—$C_{1-3}$ haloalkyl, halogen, and oxo. In some embodiments, $R^6$ in Formulas I, Ia, Ib, Ic, or Id is selected form the group consisting of $C_{1-3}$ alkyl, —O—$C_{1-3}$ alkyl, $C_{1-3}$ haloalkyl, —O—$C_{1-3}$ haloalkyl, and halogen. In some embodiments, $R^5$ is —OH, $C_{1-3}$ alkyl, or —O—$C_{1-3}$alkyl.

In some embodiments, the present invention provides a compound Formula I, wherein,

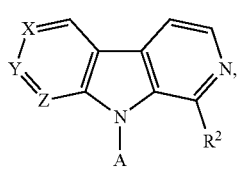
(I)

or a salt, hydrate, prodrug, or isomer thereof, wherein
$R^2$ is selected from the group consisting of H, $C_{1-6}$alkyl, and $C_{1-6}$ haloalkyl,
$R^{3c}$, if present, is H or $C_{1-6}$ alkoxy;
$R^{3b}$ or $R^{3d}$, if present, is H or halogen; and
A is

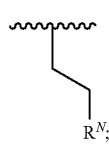

$R^N$ is heterocyclyl or heteroaryl, and wherein
X, Y, and Z, and A are as defined in Formula I as well as the subembodiments described herein.

In some embodiments, the present invention provides a compound Formula I, wherein

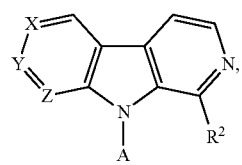
(I)

or a salt, hydrate, prodrug, or isomer thereof, wherein
$R^2$ is H, $C_{1-6}$ haloalkyl, or $C_{1-6}$ alkyl;
$R^{3c}$, if present, is $C_{1-6}$ alkoxy;
$R^{3b}$ or $R^{3d}$, if present, is H or halogen;
A is

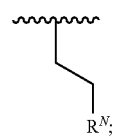

and
$R^N$ is

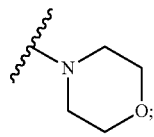 [SMILES: *N1CCOCC1]

and
wherein X, Y, and Z as are defined above.
In some embodiments of the compound of Formula Ia, Ib, Ic, or Id
$R^2$ is $C_{1-6}$ alkyl or $C_{1-6}$ haloalkyl;
$R^{3b}$, if present, is H or halogen;
$R^{3c}$ is $C_{1-6}$ alkoxy; and
$R^N$ is heterocyclyl or heteroaryl.
In some embodiments of the compound of Formula Ia, Ib, Ic, or Id
$R^2$ is $C_{1-6}$ haloalkyl;
$R^{3b}$, if present, is H or halogen;
$R^{3c}$ is $C_{1-6}$ alkoxy;
A is

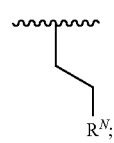

and
$R^N$ is

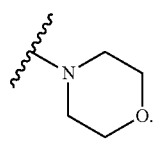 [SMILES: *N1CCOCC1]

In some embodiments of the compound of Formula Ia, Ib, Ic, or Id $R^2$ is $CF_3$; and $R^{3b}$, if present, is H or halogen;

$R^{3c}$ is methoxy; and wherein

A is

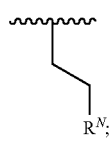

and $R_N$ is as defined in Formula I as well as the subembodiments described herein.

In one group of embodiments compounds of Formula I have a structure selected from the following:

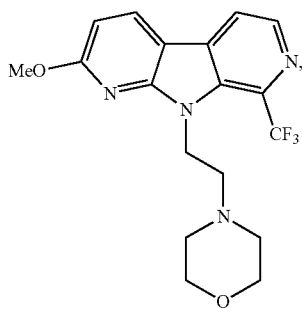

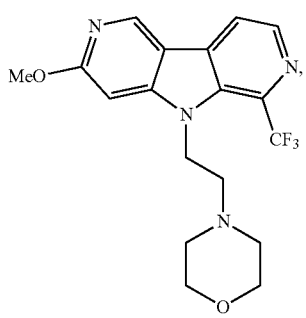

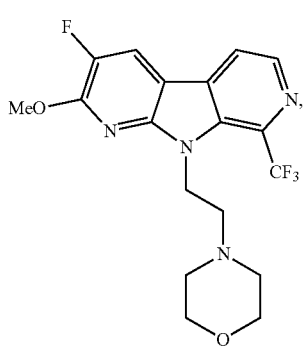

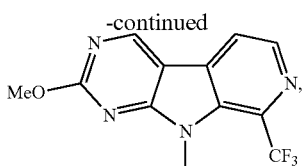

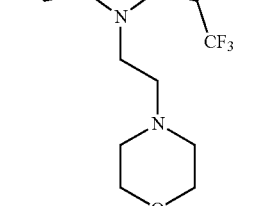

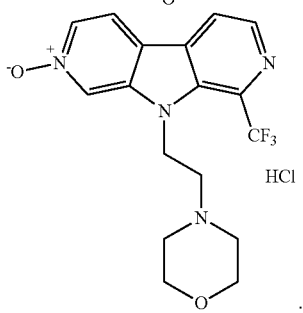

In some embodiments, the invention provides a formate salt of a compound according to any of the compounds described above. In some embodiments, the invention provides a citrate salt of a compound according to any of the compounds described above. In some embodiments, the invention provides a hydrochloride salt of a compound according to any of the compounds described above.

The compounds and compositions of the present invention can also include hydrates, solvates, and prodrug forms. The compounds and compositions of the present invention can also include the isomers and metabolites of compounds of Formula I, Ia, Ib, Ic, or Id.

In some embodiments, the invention provides a pharmaceutical composition comprising a compound according to Formula I, Ia, Ib, Ic, or Id and a pharmaceutically acceptable excipient.

The compounds of the present invention can be in the salt form. Salts include, but are not limited, to sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases include alkali metal salts such as sodium salts, and potassium salts; alkaline earth metal salts such as calcium salts, and magnesium salts; aluminum salts; and ammonium salts.

Other salts with organic bases include salts with diethylamine, diethanolamine, meglumine, and N,N'-dibenzylethylenediamine. In some embodiments, the present invention provides the hydrochloride salt.

In some embodiments, the compounds of the present invention comprise nitrogen atoms which are optionally further oxidized, i.e., the compounds are N-oxides. By way of example only, in one instance, a nitrogen atom in a pyrido-indolyl ring system in a compound of Formula I, Ia, Ib, Ic, or Id is oxidized to the corresponding N-oxide.

In some embodiments, the compounds described herein are delivered and/or formulated as prodrugs. In one embodiment, any compound described herein is an ester prodrug. In another embodiment, any compound described herein is an amide prodrug. In further embodiments, the prodrug moieties comprise conjugated groups which allow selective targeting at a bone structure. Examples of such motifs are described in Erez et al., *Bioorg. Med. Chem. Lett.* 2008, 18, 816-820 and Neale et al., *Bioorg. Med. Chem. Lett.* 2009, 19, 680-683 and are incorporated herein by reference. Accordingly, contemplated within the scope of embodiments presented herein are estradiol conjugates and/or bisphosphonate conjugates of compounds of Formula I.

The compounds of the present invention can be made by a variety of methods known to one of skill in the art (see *Comprehensive Organic Transformations* Richard C. Larock, 1989). One of skill in the art will appreciate that other methods of making the compounds are useful in the present invention. Exemplary methods for the synthesis of compounds of Formula I, are described in the Examples section and in Scheme 1 below.

Scheme 1

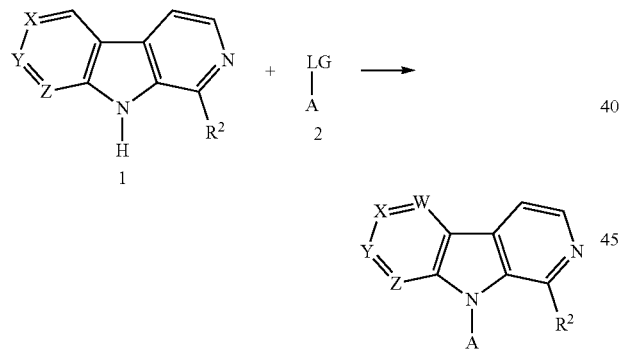

Starting with a compound 1, reaction with a compound 2 comprising a leaving group (LG) provides compounds of Formula I. Various leaving groups are suitable including and not limited to halo, activated esters, mesylates, triflates or any other suitable leaving groups which allow for the attachment of the group

at the 9-position of the core ring system. Optionally, where $R^{3c}$ is a methoxy, it can be converted to a hydroxy group by demethylation using procedures described, for example, HBr in acetic acid, or boron tribromide, or any other suitable procedure. Optionally, compounds of Formula I comprise N-oxides which are prepared by oxidation using, for example, chloroperbenzoic acid.

IV. Methods of Promoting Bone Formation

In another aspect, the present invention provides a method of promoting bone formation and fusion in a subject in need thereof, by administering to the subject a therapeutically effective amount of a compound of the present invention (e.g., a compound or composition of Formula I, Formula Ia, Formula Ib, Formula Ic, or Formula Id as described in Section III above).

In some embodiments, the present invention provides a method of promoting bone formation in a subject in need thereof, comprising administering to the subject a therapeutically effective amount of a compound of Formula I.

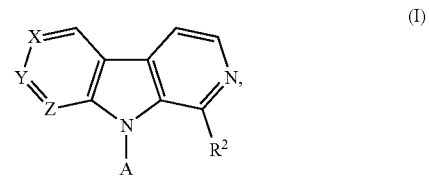

or a salt, hydrate, prodrug, or isomer thereof, wherein
X is selected from $CR^{3b}$ and N, wherein N is optionally oxidized to the corresponding N-oxide;
Y is selected from $CR^{3c}$ and N, wherein N is optionally oxidized to the corresponding N-oxide;
Z is selected from $CR^{3d}$ and N, wherein N is optionally oxidized to the corresponding N-oxide,
provided that at least one of X, Y, and Z is N or the corresponding N-oxide;
A is

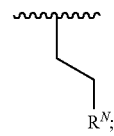

$R^N$ is selected from the group consisting of heterocyclyl and heteroaryl, wherein
the heterocyclyl moiety is selected from monocyclic, fused bicyclic, and bridged cyclic, the monocyclic heterocyclyl comprising from 4 to 7 ring members, the fused bicyclic and bridged bicyclic heterocyclyl comprising from 7 to 10 ring members, each heterocyclyl moiety having from 1 to 3 heteroatoms as ring members selected from N, O, and S, wherein each heterocyclyl moiety comprises at least one nitrogen atom as a ring member and is optionally substituted with from 1 to 3 $R^6$ moieties,
the heteroaryl moiety comprises from 5 to 10 ring members, wherein at least one ring member is a nitrogen atom and is optionally substituted with from 1 to 3 $R^6$ moieties,
each $R^2$, $R^{3b}$, $R^{3c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkyl-OH, —O—$C_{1-6}$ alkyl-OH, $C_{3-6}$ cycloalkyl-$C_{1-4}$alkoxy, and —OH;

$R^6$ is selected from the group consisting of —OH, $C_{1-3}$ alkyl, $C_{1-3}$ alkyl-OH, —O—$C_{1-3}$ alkyl, $C_{3-4}$ heteroalkyl, $C_{1-3}$ haloalkyl, —O—$C_{1-3}$ haloalkyl, halogen, and oxo.

In some embodiments, the method comprises administering to the subject a therapeutically effective amount of hydrochloride salt, sulfate salt, formate salt or a citrate salt of a compound of Formula I, Formula Ia, Formula Ib, Formula Ic, or Formula Id.

One of skill in the art will appreciate that osteoblast mineral deposit (bone formation) can be achieved by local, systemic, or both local and systemic administration. In some embodiments, bone formation is local. A subject in need of local bone formation may have any of a variety of ailments or disease states (including but not limited to, weakened bone, fractured bone, or a disease or condition characterized by low bone mass or poor mineralization as described herein). In some embodiments, the subject is in need of a spinal fusion, bone fusion, arthrodesis, or an orthopedic, dental, or periodontal synthetic bone graft or implant. In some embodiments, the present invention provides a method of promoting bone formation at a site of injury or localized condition. In some embodiments, the present invention comprises a method of fusing bones (e.g., at a site of injury). In some embodiments, the site of injury is a surgical site. In other embodiments, the injury is a fracture or weakened bone or periodontal disease.

In some embodiments, bone formation is systemic. Systemic bone formation refers to the formation of bone throughout the subject, and can affect all the bones in the subject's body. A subject in need of systemic bone formation can suffer from any of a variety of ailments or disease states. In some embodiments, the subject suffers from a low bone mass/density condition/disease (either primary or secondary), a bone fracture, a periodontal disease/condition, or a disease/condition causing poor bone mineralization (e.g., ostoegenesis imperfect or HPP). Low bone mass can be determined by a variety of methods known to one of skill in the art. For example, low bone mass/density can be characterized by a T-score less than about –0.5. Low bone mass/density diseases/conditions include, but are not limited to, osteoporosis, osteopenia, and osteoporosispseudoglioma syndrome (OPPG), glucocorticoid induced low bone mass/density, Osteogenesis imperfecta. In some other embodiments, the low bone mass condition/disease can be osteopenia or osteoporosispseudoglioma syndrome (OPPG), HPP, or glycocorticoid induced low bone mass/density or other diseases which result in secondary low bone density conditions.

Local and/or systemic bone formation using a compound or composition of the present invention can be achieved according to any of a variety of methods. Methods of formulating and administering the compounds and compositions of the present invention (e.g., a compound or composition of Formula I) are described in Section VII below. In some embodiments, the method of promoting bone formation comprises implanting a medical device as described herein (e.g., in Section VIII below) to subject in need thereof.

The methods of promoting osteoblast mineral deposits, ultimately increasing bone mineralization or density, can be used to treat diseases characterized by secondary induced osteoporosis (low bone mass) including, but not limited to, osteomalacia, Polyostotic fibrous dysplasia, osteogenesis imperfecta, Paget's disease, rheumatoid arthritis, zero gravity, osteoarthritis, Prolonged inactivity or immobility, arthrodesis, osteomyelitis, Celiac disease, Crohn's Disease, Ulcerative Colitis, inflammatory bowel disease, gastrectomy, secondary induced osteoporosis, Amennorhea, Cushing's Disease, Cushing's syndrome, Diabetes Mellitus, Diabetes, Eating Disorders, Hyperparathyroidism, Hyperthyroidism, Hyperphosphatasia (HPP), Hyperprolactinemia, Kleinefelter Syndrome, Thyroid Disease, Turner Syndrome, steroid induced osteoporosis, seizure or depression induced osteoporosis, immobility, arthritis, cancer induced secondary osteoporosis, Gonadotropin releasing hormone agonists induced low bone mass, Thyroid medication induced low bone mass, Dilantin (phenytoin), depakote induced low bone mass, chemotherapy induced low bone mass, Immunosuppressant induced low bone mass, Blood thinning agents induced low bone mass, Grave's disease, Juvenile rheumatoid arthritis, Malabsorption syndromes, Anorexia nervosa, Kidney disease, Anticonvulsant treatment (e.g., for epilepsy), Corticosteroid treatment (e.g., for rheumatoid arthritis, asthma), Immunosuppressive treatment (e.g., for cancer), Inadequate nutrition (especially calcium, vitamin D), Excessive exercise leading to amenorrhea (absence of periods), Smoking, and Alcohol abuse, pregnancy-associated osteoporosis, copper deficiency, Dibasic aminoaciduria type 2, Werner's syndrome, Hajdu-Cheney syndrome, Hyperostosis corticalis deformans juvenilis, Methylmalonic aciduria type 2, Cystathionine beta-synthase deficiency, Exemestane, Hyperimmunoglobulin E (IgE) syndrome, Haemochromatosis, Singleton-Merten syndrome, Beta thalassaemia (homozygous), Reflex sympathetic osteodystrophy, Sarcoidosis, Winchester syndrome, Hallermann-Streiff syndrome (HSS), Cyproterone, Glycerol kinase deficiency, Bonnet-Dechaume-Blanc syndrome, Prednisolone, Heparin, Geroderma osteodysplastica, Torg osteolysis syndrome, Orchidectomy, Fabry's disease, Pseudoprogeria syndrome, Wolcott-Rallison syndrome, Ankylosing spondylitis, Myeloma, Systemic infantile hyalinosis, Albright's hereditary osteodystrophy, Anorexia Nervosa, Autoimmune Lymphoproliferative Syndrome, Brown-Sequard Syndrome, Diamond-Blackfan anemia, Eating disorders, Galactorrhoea-Hyperprolactinaemia, Gonadal dysgenesis, Kidney conditions, Menkes Disease, Menopause, Neuritis, Ovarian insufficiency due to FSH resistance, Familial Ovarian insufficiency, Premature aging, Primary biliary cirrhosis, Prolactinoma, Familial Prolactinoma, Renal osteodystrophy, Ulcerative colitis, Underweight, Werner syndrome, Bone tumor, Bone cancer, Brittle bone disease, Osteonecrosis, Osteogenesis imperfecta congenita, Osteogenesis imperfecta tarda, osteogenesis imperfecta, glucocorticoid induced osteopenia/osteoporosis and periodontal disease. One of skill in the art will appreciate that other types of conditions, diseases and treatments also lead to osteoporosis.

Bone formation can be measured according to any of a variety of ways known to one of skill in the art. Methods of measuring bone formation include, but are not limited to, uCT (micro CT), Dual X-ray absorption (Bone density), ultrasound, QCT, SPA, DPA, DXR, SEXA, QUS, X-ray, using the human eye during surgically manipulation, Alizarin red S, serum osteocalcin, serum alkaline phosphatase, Serum bone Gla-protein (BGP), bone mineral content, bone ash weight, serum calcium, serum phosphorus, tantalum markers, and serum IGF-1.

Many indicators of bone formation can be used to measure and/or quantify the amount of bone formation, including bone density. In some embodiments, bone formation can be demonstrated by an increase of 0.1% in bone density. In other embodiments, bone growth can be demonstrated by an increase of 0.2%, 0.3%, 0.4%, 0.5%, 0.6%, 0.7%, 0.8%, 0.9%, 1%, 2%, 3%, 4%, 5%, 6%, 7%, 8%, 9%, 10%, 12%, 14%, 16, 18%, 20%, 30%, 40%, 50%, 60%, 70%, 80%, 90%, 100%, 200%, 300%, 400%, 500%, 600%, 700%, 800%, 900% or 1000% or greater, in bone density. Bone density can be measured by a variety of different methods, including the T-score and Z-score. The Z-score is the number of standard deviations above or below the mean for the patient's age and sex. The T-score is the number of standard deviations above or below the mean for a healthy 30 year old adult of the same sex as the patient. Low bone mass is characterized by a T-score of −1 to −2.5. Osteoporosis is characterized by a T-score less than −2.5. Improvement in the T-score or Z-score indicate bone growth. Bone density can be measured in a variety of places of the skeleton, such the spine or the hip. One of skill in the art will appreciate that other methods of determining bone density are useful in the present invention.

V. Methods of Treating Renal Damage

In another aspect, the present invention provides a method of treating renal damage by administering to a subject suffering from renal damage, a therapeutically effective amount of a compound of the present invention (e.g., a compound or composition of Formula I, as described in Section III above).

Renal damage can be caused by a variety of ailments known to one of skill in the art. In some embodiments, renal damage is caused by infection, radiation, toxin, dehydration or trauma. Toxins causing renal damage include, but are not limited to, chemicals, poisons, and chemotherapeutic agents. One of skill in the art will appreciate that other causes of renal damage can be treated by the methods of the present invention.

Renal damage treatable by the compounds of the present invention includes acute renal failure. Acute renal failure is also known as acute kidney failure or acute kidney injury. Acute renal failure results in retention of nitrogenous (urea and creatinine) and non-nitrogenous waste products that are normally excreted by the kidney. Depending on the severity and duration of the renal dysfunction, this accumulation is accompanied by metabolic disturbances, such as metabolic acidosis (acidification of the blood) and hyperkalaemia (elevated potassium levels), changes in body fluid balance, and effects on other organ systems. Acute renal failure can be characterized by oliguria or anuria (decrease or cessation of urine production), although nonliguric acute renal failure can also occur.

A subject can be characterized as being at (1) a risk for acute damage; (2) kidney damage resulting in injury; (3) acute renal failure; and (4) loss of kidney function. Risk for acute kidney damage is characterized by serum creatinine increased 1.5 times or urine production of <0.5 ml/kg body weight over 6 hours. Injury is reached when serum creatinine increased 2.0 times or urine production <0.5 ml/kg over 12 hours. Failure is reached when serum creatinine increased 3.0 times or creatinine >355 μM (with a rise of >44) or urine output below 0.3 ml/kg over 24 hours. Loss of kidney function is reached when a subject suffers from persistent acute renal failure or more than four weeks of complete loss of kidney function.

Kidney biopsy can be performed in the setting of acute renal failure, to provide a definitive diagnosis and sometimes an idea of the prognosis, unless the cause is clear and appropriate screening investigations are reassuringly negative.

Renal therapeutic agents of the invention can be used in subjects that have received renal injury, or those at risk of chronic renal failure. As used herein, a subject is said to be in, or at risk for, chronic renal failure, or at risk of the need for renal replacement therapy (i.e., chronic hemodialysis, continuous peritoneal dialysis, or kidney transplantation), if the subject is reasonably expected to suffer a progressive loss of renal function associated with progressive loss of functioning nephron units. Whether a particular subject is in, or at risk of, chronic renal failure is a determination which may routinely be made by one of ordinary skill in the relevant medical or veterinary art. Subjects in, or at risk of, chronic renal failure, or at risk of the need for renal replacement therapy, include but are not limited to the following: subjects which can be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, renal cell carcinoma, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min 30 ml/min or 20 ml/min; human female subjects weighing at least about 40 kg and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

VI. Methods of Treating Diabetes

The compounds and compositions of the present invention are also useful in the treatment of diabetes. Accordingly, some embodiments of the invention provide a method of treating diabetes. The method includes administering to a subject in need thereof a therapeutically effective amount of a compound of the present invention (e.g., a compound or composition of Formula I, Formula Ia, Formula Ib, Formula Ic, or Formula Id as described in Section III above).

Diabetes is a disease where the body is unable to produce any or enough insulin causing elevated blood glucose levels in afflicted individuals. Without being bound to any particular theory, it is believed that the compounds and compositions of the present invention help to treat diabetes by regenerating pancreatic cells. In some embodiments, the compounds of the present invention are believed to induce regeneration of beta cells in the pancreas. See, for example, Wang P. et al., *Nat Med.*, 21(4):383-388 (2015).

Diabetic therapeutic agents of the invention can be used in subjects that have received a pancreatic injury, are in a pre-diabetic state or are diabetic. As used herein a subject that is said to have received pancreatic injury is one that has reduced, compromised, or no native production of insulin. Whether a subject is considered pre-diabetic or diabetic depends on a number of factors including the subjects fasting blood glucose level. A subject is considered pre-diabetic with a fasting blood glucose level is above 100 mg/dL. A subject is considered diabetic if the subjects fasting blood glucose level is above 125 mg/dL.

Pancreatic injury can be caused by a variety of ailments known to one of skill in the art. In some embodiments, pancreatic damage is caused by infection, autoimmune disease, radiation, toxin, or trauma. Toxins causing pancreatic include, but are not limited to, chemicals, poisons, and chemotherapeutic agents. One of skill in the art will appreciate that other causes of pancreatic damage can be treated by the methods of the present invention.

In some embodiments, the disease being treated is Type 1 Diabetes. In some embodiments, the disease being treated is Type 2 Diabetes.

The compounds of the present invention may be administered in series or in combination with other therapeutic agents useful in treating diabetes. In some embodiments, the other therapeutic agents are antidiabetic agents. Diabetic agents include, but are not limited to, lipid-lowering/lipid-modulating agents, agents for treating diabetic complications, anti-obesity agents, antihypertensive agents, SGLT1 inhibitors, SGLT2 inhibitors, antihyperuricemic agents, and agents for treating chronic heart failure, atherosclerosis or related disorders.

VII. Methods of Treating Bone Loss

In another aspect, the present invention provides a method of treating bone loss by administering to a subject suffering from bone loss, a therapeutically effective amount of a compound of the present invention (e.g., a compound or composition of Formula I, Formula Ia, Formula Ib, Formula Ic, or Formula Id as described in Section III above).

As diagrammed in FIG. 1, bone density in an individual can be described by the net loss (bone resorption) and gain (bone formation) of bone mass. In individuals with bone loss, the net bone resorption is greater than the bone formation causing a decrease in bone loss. It is contemplated that in particular embodiments of this invention, bone loss may be treated by inhibiting or reducing bone resorption while stimulating or encouraging bone formation.

Antiresorptive agents are compounds which slow the process of bone resorption. Antiresorptive agents include, but are not limited to, RankL inhibitors, Denosumab, Prolia, Cathepsin-K modulators, Alendronate, Fosamax, selective estrogen receptor modulators (SERMS), Calcium, Estrogen, Bisphosphonates, and Calcitonin.

The compounds and compositions of the present invention treat bone loss by promoting bone formation. When the compounds of the present invention are administered sequentially or combination with one or more antiresorptive agents, both the rate of bone resorption is inhibited or reduced and the rate of bone formation is stimulated.

The compounds and compositions of the present invention and the antiresorptive agents described herein may be administered sequentially or in combination. Further details of combination therapy are discussed in section IX. C., below.

The compounds and compositions of the present invention treat bone loss by promoting bone formation. In some embodiments, when the compounds of the present invention are administered sequentially with one or more antiresorptive agents, the rate of bone resorption is inhibited or reduced and the amount of bone formation is maintained.

The compounds and compositions of the present invention may be administered to patients who have been treated with an antiresorptive, thus serially, or patients may be administered sequentially with one or more antiresorptive agents, whereby the rate of bone resorption is inhibited or reduced and the amount of bone formation is maintained.

VII. Methods of Treating Cancer

The compounds and compositions of the present invention are also useful in the treatment of cancer. Accordingly, some embodiments of the invention provide a method of treating cancer. The method includes administering to a subject in need thereof a therapeutically effective amount of a a compound of the present invention (e.g., a compound or composition of Formula I, Formula Ia, Formula Ib, Formula Ic, or Formula Id as described in Section III above).

In some embodiments, the compounds of the present invention are useful in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29, Saos-2, HeLa or MCF-7, or by showing inhibition of a CDK enzyme (such as CDK2 or CDK4), MTT or BRDU in an appropriate assay. Using such cell line and enzymes assays it may be determined whether a compound is anti-proliferative in the context of the present invention.

As used herein, the term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. One of skill in the art will appreciate that other cancers and proliferative disorders can be treated by the compounds and compositions of the present invention.

In some embodiments, the cancer is bone cancer, colon cancer, multiple myeloma, gastric cancer, colorectal cancer, prostate cancer, cervical cancer, lung cancer, pancreatic cancer, medulloblastoma, liver cancer, parathyroid cancer, endometrial cancer, or breast cancer. In some embodiments, the cancer is bone cancer. In some embodiments, the cancer is a cancer that is characterized by secondary low bone mass, including but not limited to, breast cancer and prostate cancer. In some embodiments, the cancer is a cancer that has metastasized to bone.

IX. Formulation and Administration

In some embodiments, the present invention provides a pharmaceutical composition including a compound as described herein (e.g., a compound or composition of Formula I, as described in Section III above) and a pharmaceutically acceptable excipient. In other embodiments, the composition further comprises an osteoconductive matrix.

The compositions of the present invention can be in the form of a pharmaceutical composition containing the antagonist and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters. The selection of a pharmaceutically acceptable carrier will depend, in part, on the chemical nature of the compound.

The compounds of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra).

A pharmaceutically acceptable carrier may include physiologically acceptable compounds that act, for example, to stabilize the composition or increase its absorption, or other excipients as desired. Physiologically acceptable compounds include, for example, carbohydrates, such as glucose, sucrose, dextrans, dextrins, cyclodextrins, or captisol, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration and on its particular physiochemical characteristics.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose dextrans, dextrins, cyclodextrins, or captisol, chelating agents such as EDTA, glutathione and other stabilizers and excipients. Neutral buffered saline or saline mixed with nonspecific serum albumin are exemplary appropriate diluents.

The amount of a compound or composition of the present invention (e.g., a compound or composition of Formula I, as described herein) that is administered to an individual will depend, in part, on the disease and/or extent of injury. Methods for determining an effective amount of an agent to administer for a diagnostic or a therapeutic procedure are well known in the art and include phase I, phase II and phase III clinical trials, or the Pilot and Pivotal trials (FDA device approval pathway). Generally, an agent is administered in a dose of about 0.0001 to 500 mg/kg body weight when administered systemically, and at a concentration of approximately 0.1 nM to 1000 µM when administered directly to a wound site.

The total amount of the compound or composition can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a particular compound or composition that is needed to provide an effective amount to a region or regions of injury depends on many factors, including the age and general health of the subject as well as the route of administration, the number of treatments to be administered, and the nature of the compound. In view of these factors, the skilled artisan would adjust the particular dose so as to obtain an effective amount for efficaciously promoting bone formation for therapeutic purposes.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, transdermal patches, ampoules, and powders in vials, ampoules, or on an osteoconductive matrix. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

In some embodiments, the methods of the present invention include application of the compounds as described herein in cocktails including other medicaments, for example, antibiotics, fungicides, anabolic bone agents, antiresoptive agents, and/or anti-inflammatory agents. Alternatively, the methods may comprise sequential dosing of an afflicted individual with a compound as described herein and one or more additional medicaments to optimize a treatment regime. In such optimized regimes, the medicaments, including the compounds of this invention, can be applied in any sequence and in any combination.

Individuals to be treated with the compounds and compositions of the present invention can be any mammal, for example, a human or a non-human mammal, e.g., a primate, dog, cat, horse, cow, goat, sheep, pig, mouse, or rat, or any commercially important animal or domesticated animal.

In some embodiments, an individual to be treated according to the methods of the present invention is an individual who has received or is receiving an antiresorptive therapeutic agent. For example, in some embodiments, antiresorptive therapy may be administered concurrently with a compound or composition of the present invention. In some embodiments, antiresorptive therapy and therapy with a compound or composition of the present invention are administered sequentially (either antiresorptive therapy preceding therapy with a compound or composition of the present invention, or therapy with a compound or composition of the present invention preceding antiresorptive therapy). In some embodiments, the individual may have been previously treated with an antiresorptive agent. In some embodiments, an individual may be concurrently treated with an antiresorptive agent during a first portion of the treatment course for the compound or composition of the present invention but may discontinue treatment with the antiresorptive agent during a second portion of the treatment course. In some embodiments, an individual to be treated according to the methods of the present invention has not been treated with an antiresorptive agent. In some embodiments, an individual is treated with an antiresorptive agent after being treated with a compound or composition of the present invention.

In some embodiments, an individual to be treated according to the methods of the present invention is an individual who has received or is receiving a combination of antiresorptive and/or bone anabolic therapeutic agents. For example, in some embodiments, antiresorptive and/or bone anabolic therapy may be administered concurrently with a compound or composition of the present invention. In some embodiments, antiresorptive and/or bone anabolic therapy and therapy with a compound or composition of the present invention are administered sequentially (either antiresorptive therapy preceding therapy with a compound or composition of the present invention, or therapy with a compound or composition of the present invention preceding antiresorptive therapy). In some embodiments, the individual may have been previously treated with an antiresorptive and/or bone anabolic agent. In some embodiments, an individual may be concurrently treated with an antiresorptive and/or bone anabolic agent during a first portion of the treatment course for the compound or composition of the present invention but may discontinue treatment with the antiresorptive and/or bone anabolic agent during a second portion of the treatment course. In some embodiments, an individual to be treated according to the methods of the present invention has not been treated with an antiresorptive agent and/or bone anabolic. In some embodiments, an individual is treated with an antiresorptive and/or bone anabolic agent after being treated with a compound or composition of the present invention.

In some embodiments, the compounds and compositions of the present invention are administered systemically. In some embodiments, the compounds and compositions of the present invention are administered locally.

A. Systemic Delivery

In some embodiments, the compounds and compositions of the present invention are administered systemically. Systemic administration of the compounds and compositions of the present invention can be used, for example, for the treatment of a systemic disease or condition characterized by whole body effects, i.e., low bone mass (e.g., osteoporosis), diabetes, cancer, or kidney disease.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, transdermal, intracavernous, intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The pharmaceutical forms can include one or more of lactose, sucrose, mannitol, sorbitol, calcium phosphates, corn starch, potato starch, dextrans, dextrins, cyclodextrins, captisol, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, pharmaceutically compatible carriers, and other ingredients categorized by the FDA as inert ingredients. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Particular oral formulations suitable for the present invention include, but are not limited to, buffered aqueous solutions from pH 4 to 10; unbuffered aqueous systems from pH 2 to 10; cosolvent aqueous solutions comprising propylene glycol, glycerol, ethanol, or combinations thereof, aqueous solutions comprising one or more emulsifying agents such as one or more saturated polyglycolysed glycerides (e.g. Gelucire©); aqueous suspensions comprising methylcellulose (optionally including sodium dodecyl sulfate, sodium laurel sulfate, docusate, or polysorbate 80 at sub-critical micelle concentrations (CMC)); aqueous solutions comprising a cyclodextrin (e.g. hydroxypropyl-β-cyclodextrin or sulfobutyl ether-O-cyclodextrin); solutions comprising one or more vegetable oils (e.g. safflower oil, soybean oil, oleic acid, etc.); non-aqueous solutions with or without emulsifying agents such as PEG400 or 600, soybean oil/polysorbate 80/sorbitan fatty acid ester (Span 80), mono/diglyceride or capric/caprilic acid (IMWITOR 742)/polysorbate 80 (70:30), polyethoxylated palm kernel oil/polyethylene glycol (PEG) 400 or 600/water; an aqueous surfactant solution comprising polysorbate 80 and SDS or SLS; oil suspensions comprising soybean oil and safflower oil; and preparing a compound or composition of the present invention in nanoparticles.

Formulations suitable for intravenous bolus injection of the compound or composition include, but are not limited to, aqueous solutions comprising buffered or unbuffered saline, optionally including dextrose; cosolvent systems comprising glycerin, ethanol, propylene glycol, PEG 300 or 400, glycofural, N-methylpyrrolidone (NMP), dimethylacetamide (DMA), dimethylformamide (DMF), dimethylisosorbide (DMI), dimethylsulphoxide (DMSO), or a combination thereof in water; aqueous surfactant solutions comprising polysorbate 80; aqueous solutions comprising a cyclodextrin (e.g. hydroxypropyl-β-cyclodextrin or sulfobutyl ether-β-cyclodextrin); oily emulsions; plasma; and aqueous suspensions optionally comprising methylcellulose and/or sodium dodecyl sulfate, sodium laurel sulfate, docusate, or polysorbate 80 at sub-critical micelle concentrations (CMC))

Formulations suitable for intravenous infusion of the compound or composition include, but are not limited to, aqueous solutions comprising buffered or unbuffered saline, optionally including dextrose, mannitol, or lactose; or any of the above listed formulations for intravenous bolus injection.

Formulations suitable for intramuscular, subcutaneous, or intraperitoneal administration include, but are not limited to, solutions in oil comprising soybean oil, peanut oil, sesame oil, ethyl oleate, isopropyl myristate, polysorbate 80, or sorbitan fatty acid ester; aqueous suspensions comprising water, buffered or unbuffered saline, or dextrose (in water); or any of the above listed formulations for intravenous bolus injection.

Formulations suitable for ocular administration include, but are not limited to, buffered or unbuffered aqueous solutions from pH 4 to 9 such as saline, optionally the aqueous solution may include hydroxyethyl cellulose; aqueous suspensions; or oily emulsions comprising, for example, mineral oil, peanut oil, or petrolatum.

Typical formulations for topical/transdermal administration include creams, ointments, sprays, lotions, and patches. Topical/transdermal formulations of the present disclosure comprise propylene glycol, isopropyl mystate, PEG 300, PEG 400, petroaltum or mixtures thereof, optionally ethanol or isopropanol may also be included.

The compounds of the present invention may also be included in slow release formulations for prolonged treatment following a single dose. In one embodiment, the formulation is prepared in the form of microspheres. The nanoparticle/microspheres can be prepared as a homogenous matrix of a compound with a biodegradable controlled release material, with optional additional medicaments as the treatment requires. The nanoparticle/microspheres are preferably prepared in sizes suitable for infiltration and/or injection, and injected systemically, or directly at the site of treatment.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, captisol, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone. methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

B. Local Delivery

In some embodiments, the compounds and compositions of the present invention are administered locally. Local administration of the compounds and compositions of the present invention can be used, for example, for fracture healing, fusion (e.g., arthrodesis), orthopedic reconstruction, and periodontal repair. In some embodiments, local administration comprises administering a compound or composition in conjunction with a suitable carrier material capable of maintaining the compound at an in vivo site of application or capable of providing structural load. In some embodiments, the carrier is biocompatible, a matrix, in vivo biodegradable or resorbable, and/or porous enough to allow cell infiltration. In some embodiments, a compound or composition of the present invention (e.g., a compound or composition of Formula I) is administered locally via an implantable medical device.

The compounds and compositions of the present invention are useful in clinical applications in conjunction with a suitable delivery or support system (e.g., a scaffold or matrix as described herein). As disclosed herein, the matrix can be combined with a compound or composition of Formula I to induce bone formation reliably and reproducibly in a mammalian body. The matrix preferably includes particles of porous materials. The pores are preferred to be of a dimension to permit progenitor cell migration into the matrix and subsequent differentiation and proliferation. In some embodiments, the pore size of the matrix is at least 5 μm, e.g., at least 5, 10, 15, 20, 25, 30, 40, 50, 60, 70, 80, 90, 100, 125, 150, 175, 200, 250, 300, 400, 450, 500, 550, 600, 650, 700, 750, 800, 850, 900, 950, 1000, 1200, 1500, 1700, or 2000 μm. The matrix can be fabricated by close packing particulate material into a shape spanning the bone defect, or by otherwise structuring as desired a material that is biocompatible, and preferably biodegradable or resorbable in vivo to serve as a "temporary scaffold" and substratum for recruitment of migratory progenitor cells, and as a base for their subsequent anchoring and proliferation. In some embodiments, the scaffold or matrix comprises a mesh structure, a foam structure, a sponge structure, or a fiber structure.

A scaffold or matrix for use in delivering a compound of the present invention can comprise a synthetic, a biologic material, or a combination thereof. In some embodiments, the scaffold or matrix comprises a naturally occurring polymer, a synthetic biodegradable polymer, a synthetic nonbiodegradable polymer, a bioceramic, a bioglass, or combinations thereof. Natural and synthetic polymers, bioceramics, and bioglasses for use in scaffolds are known in the art. See, e.g., Dhandayuthapani et al., International Journal of Polymer Science, volume 2011, article ID 290602 (2011), incorporated by reference herein. Natural polymers include, but are not limited to, proteins (e.g., silk, collagen, gelatin, fibrinogen, elastin, keratin, actin, and myosin), polysaccharides (e.g., cellulose, amylose, dextran, chitin, chitosan, and glycosaminoglycans), and polynucleotides (e.g., DNA and RNA). Synthetic polymers include, but are not limited to, PLA, PGA, PLLA, PLGA, PCL, PLDLA, PDS, PGCL, PEA, PCA, PDLLA, PEU, and PBT. Bioceramics and bioglasses include, but are not limited to, HAP, TCP, CP ceramics, BCP, and TCP. In some embodiments, the scaffold or matrix is a hydrogel scaffold, a fibrous scaffold, a microsphere scaffold, a polymer-bioceramic composite scaffold, or an acellular scaffold.

In some embodiments, the scaffold or matrix is an osteoconductive matrix. Non-limiting examples of suitable osteoconductive matrix materials include, for example, collagen; homopolymers or copolymers of glycolic acid, lactic acid, and butyric acid, including derivatives thereof; and ceramics, hydroxyapatite, tricalcium phosphate, biphasic calcium phosphate and other calcium phosphates, and calcium sulphates, or combinations thereof. Typically, osteoconductive matricies contemplated herein include at least one of the previously listed materials. Other matrices useful in the present invention include, but are not limited to, biocomposite bone grafts, Kryptonite bone cement (Doctors Research Group, Oxford, CT), Vitoss, Vitoss BA, Orthoblend, Grafton, Arthrex, Allograft, Cadaverbone, Ostoset, Novabone, Augmatrix, Mastergraft, Hydroset, Prodense, Pro-stim, hydroset, (porous) tantalum bone graft, titanium mesh, titanium bone graft, and Genex bone graft. Combinations of these matrix materials also can be useful. The osteoconductive matrix can also include a structural support such as a calcium salt, calcium sulfate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a bioactive glass, a biocompatible ceramic, a calcium phosphate ceramic, polytetrafluoroethylene, sulfate salt, collagen, homopolymers or copolymers of glycolic acid, lactic acid, and butyric acid, including derivatives thereof; and ceramics, hydroxyapatite, tricalcium phosphate, biphasic calcium phosphate and other calcium phosphates, and calcium sulphates. Other matrices useful in the present invention include, but are not limited to, biocomposite bone grafts, Kryptonite bone cement (Doctors Research Group, Oxford, CT), Vitoss, Vitoss BA, Orthoblend, Grafton, Arthrex, Allograft, Cadaverbone, Ostoset, Novabone, Augmatrix, Mastergraft, Hydroset, Pro-dense, Pro-stim, hydroset, (porous) tantalum bone graft, titanium mesh, titanium bone graft, Genex bone graftor hydrogel.

In some embodiments, the osteoconductive matrix comprises an osteoinductive agent and, optionally, a structural support. The osteoinductive agent can be any agent that promotes bone formation. In some embodiments, the osteoinductive agent is bone allograft, bone autograft, demineralized bone, or periodontal ligament cells.

C. Combination Therapy

In practicing the methods of the present invention, the pharmaceutical compositions can be used alone, or in combination with other therapeutic or diagnostic agents. Additionally, the medical devices described herein include the use of the compound of Formula I alone or in combination with an other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

In some embodiments, a compound or composition as described herein (e.g., a compound or composition of Formula I) is administered in combination with one or more other therapeutic agents. When a compound of the present invention and is combined with another agent, the two can be co-administered or administered separately. Co-administration includes administering the other agent within 0.5, 1, 2, 4, 6, 8, 10, 12, 16, 20, or 24 hours, as well as within 1 to 7 days (e.g., 1, 2, 3, 4, 5, 6, or, 7 days), 1 to 4 weeks (e.g., 1, 2, 3, or 4 weeks), or 1 or 18 months (e.g., 1, 2, 3, 4, 5, 6, 7, 8, 9, 10, 11, 12, 13, 14, 15, 16, 17, or 18 months) of administering the compound of the present invention. Co-administration also includes administering the other agent and the compound of the present invention simultaneously, approximately simultaneously (e.g., within about 1, 5, 10, 15, 20, or 30 minutes, or on the same day, or on the same week, or on the same month of each other), or sequentially in any order. In some embodiments, co-administration comprises administering another agent (e.g., an antiresorptive) for a period of time (e.g., weeks, months, or years), then administering a compound or composition of Formula I for a period of time (e.g., days, weeks, months, or years), then administering the other agent (e.g., antiresorptive) either alone or in combination with the compound or composition of Formula I. In some embodiments, the other agent and the compound of the present invention can each be administered once a day, or two, three, or more times per day so as to provide the preferred dosage level per day.

In some embodiments, co-administration can be accomplished by co-formulation, i.e., preparing a single pharmaceutical composition including both a compound of the present invention and the second therapeutic agent (e.g., the antiresorptive agent). In other embodiments, the compound of the present invention and the second therapeutic agent are formulated separately.

The one or more other therapeutic agents can be delivered by any suitable means. The pharmaceutical preparation is preferably in unit dosage form. In such form the preparation is subdivided into unit doses containing appropriate quantities of the antiresorptive agent and/or the compound of the present invention. The unit dosage form can be a packaged preparation, the package containing discrete quantities of preparation, such as packeted tablets, capsules, and powders in vials or ampoules. Also, the unit dosage form can be a capsule, tablet, cachet, patch, or lozenge itself, or it can be the appropriate number of any of these in packaged form.

The one or more other therapeutic agents can be present in any suitable amount, and can depend on various factors including, but not limited to, weight and age of the subject, state of the disease, etc. Suitable dosage ranges for the one or more other therapeutic agents in combination with the a compound or composition of the present invention include from about about 0.0001 ug to about 10,000 mg, or about 0.0001 ug to about 1000 mg, or about 0.0001 ug to about 500 mg, or about 0.0001 ug to about 1000 ug, 0.1 ug to about 10,000 mg, or about 0.1 ug to about 1000 mg, or about 0.1 ug to about 500 mg, or about 0.1 ug to about 1000 ug or about 1 ug to about 1000 mg, or about 1 ug to about 500 mg, or about 1 ug to about 50 mg, or about 1 ug to about 1000 ug, or about 10 ug to about 1000 mg, or about 10 ug to about 500 mg, or about 10 ug to about 50 mg, or about 0.1 mg to about 10,000 mg, or about 1 mg to about 1000 mg, or about 10 mg to about 750 mg, or about 25 mg to about 500 mg, or about 50 mg to about 250 mg. Suitable dosages for the one or more other therapeutic agents in combination with a compound or composition of the present invention, include about 0.01, 0.1, 1, 5, 10, 20, 30, 40, 50, 60, 70, 80, 90, 100, 200, 300, 400, 500, 600, 700, 800, 900, 1000, 1250, 1500, 1750 or 2000 mg.

The one or more other therapeutic agents and the compound or composition of the present invention can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w) or about 1:1 (w/w). Other dosages and dosage ratios of the antiresorptive agent and the compound of the present invention are suitable in the compositions and methods of the present invention.

The composition can also contain other compatible therapeutic agents. The compounds described herein can be used in combination with one another, with other active agents, or with adjunctive agents that may not be effective alone, but may contribute to the efficacy of the active agent.

In some embodiments, an individual to be treated according to a method of the present invention is administered a compound or composition as described herein (e.g., a compound or composition of Formula I, Formula Ia, Formula Ib, Formula Ic, or Formula Id as described herein) in combination or sequentially with an antiresorptive drug. Antiresorptive drugs include those that slow or block the resorption of bone. Administration of a compound or composition as described herein and an antiresorptive drug can promote local bone growth and/or systemic bone growth. In some embodiments, the administration of a compound compound or composition as described herein and an antiresorptive drug promotes systemic bone growth. Bone growth can be achieved by increasing bone mineral content, increasing bone density and/or growth of new bone. In other embodiments, local application of the compound or composition as described herein and an antiresorptive drug achieves systemic bone growth.

Antiresorptive drugs useful in the methods of the present invention include, but are not limited to, denosumab, Prolia, a RankL inhibitor, a bisphosphonate (e.g., Fosamax, denosumab, Prolia, Actonel, or Reclast, Alendronate, Bonviva™, Zometa™, olpadronate, neridronate, skelid, bonefos), a selective estrogen receptor modulator (SERM) or analog (e.g., Evista), calcitonin, a calcitonin analog (e.g., Miacalcic), parathyroid hormone, calcilytics, calcimimetics (e.g., cinacalcet), statins, anabolic steroids, lanthanum and strontium salts, and sodium fluoride, Vitamin D or a Vitamin D analog, CatK inhibitor, prostaglandin inhibitor, or phosphodiesterase inhibitor type E.

In some embodiments, the antiresorptive drug is denosumab.

Bisphosphonates useful in the methods of the present invention can be any suitable bisphosphonate. In some embodiments, the bisphosphonates are nitrogenous, such as Pamidronate (APD, Aredia), Neridronate, Olpadronate, Alendronate (Fosamax), Ibandronate (Boniva), Risedronate (Actonel) and Zoledronate (Zometa). In other embodiments, the bisphosphonates are non-nitrogenous, such as Etidronate (Didronel), Clodronate (Bonefos, Loron) and Tiludronate (Skelid). One of skill in the art will appreciate that other bisphosphonates are useful in the present invention.

SERMs useful in the methods of the present invention can be any suitable SERM. In some embodiments, the SERM can be clomifene, raloxifene, tamoxifen, toremifene, bazedoxifene, lasofoxifene or ormeloxifene. One of skill in the art will appreciate that other SERMs are useful in the present invention.

The antiresorptive drug can also be any suitable calcitonin analog or cathepsin K inhibitor. In some embodiments, calcitonin analogs useful in the methods of the present invention include, but are not limited to, miacalcic. One of skill in the art will appreciate that other calcitonin analogs are useful in the present invention.

Vitamin D analogs useful in the methods of the present invention can be any suitable Vitamin D analog. In some embodiments, Vitamin D analogs useful in the methods of the present invention include, but are not limited to, Vitamin D1 (molecular compound of ergocalciferol with lumisterol, 1:1), Vitamin D2 (ergocalciferol or calciferol), Vitamin D3 (cholecalciferol), Vitamin D4 (22-dihydroergocalciferol) and Vitamin D5 (sitocalciferol). One of skill in the art will appreciate that other Vitamin D analogs are useful in the present invention.

RankL inhibitors useful in the present invention include any compounds that inhibit the activity of RankL. For example, RankL inhibitors include, but are not limited to, the human monoclonal antibody denosumab or prolia. One of skill in the art will appreciate that other RankL inhibitors are useful in the present invention.

In some embodiments, an individual to be treated according to a method of the present invention is administered a compound or composition as described herein (e.g., a compound or composition of Formula I, Formula Ia, Formula Ib, Formula Ic, or Formula Id as described herein) in combination or sequentially with an anabolic agent. Anabolic agents include, but are not limited to, parathyroid hormone (PTH) or an analog thereof, sclerostin inhibitors, bone morphogenic protein (BMP) or a BMP agonist, a population of bone marrow stem cells, or a population of mesenchymal stem cells.

In some embodiments, the anabolic agent is parathyroid hormone (PTH) or an analog thereof (e.g., teriparatide (Forteo). In some embodiments, the anabolic agent is a sclerostin antibody (Mab) inhibitor. In some embodiments, the BMP is selected from the group consisting of BMP2, BMP7, BMP4. In some embodiments, the BMP agonist is a compound described in Vrijens K, et al. PLoS One. 2013; 8(3):e59045, the contents of which is incorporated by reference for all purposes. In some embodiments, the anabolic agent is a population of bone marrow stem cells. In some embodiments, the anabolic agent is a population of mesenchymal stem cells.

X. Medical Devices

In some embodiments, the present invention provides a medical device formed from a structural support, wherein an implantable portion of the structural support is adapted to be permanently implanted within a subject, wherein the implantable portion is attached to a bone, the structural support bearing at least a partial coating including a compound of Formula I, as described herein (e.g., in Section III above). In some embodiments, the medical device is an orthopedic or periodontal medical device.

Other aspects of the present invention are directed towards medical implants. Such medical devices and implants include, for example, the osteogenic devices and methods of using the same for repairing endochondral bone and osteochondral defects taught in US patent application publication No. 20060177475 to David Rueger et al., published Aug. 10, 2006, as well as in issued U.S. Pat. Nos. 6,190,880, 5,344,654, 5,324,819, 5,468,845, 6,949,251, 6,426,332 and 5,656,593, and U.S. Publication Nos. 2002/0169122, 2002/0187104, 2006/0252724 and 2007/0172479, the subject matter of which is hereby incorporated by reference.

These medical devices generally provide a structural support having an implantable portion preferentially adapted to mechanically engage bone and/or cartilage as taught, for instance, in U.S. Publication No. 2006/0178752 to Joseph Vaccarino III, et al., published Aug. 10, 2006, the subject matter of which is hereby incorporated by reference. These bone implants desirably comprise an active agent on at least a portion thereof. As shown by U.S. Publication No. 2006/0188542 to John Dennis Bobyn, et al., published Aug. 24, 2006, the subject matter of which is hereby incorporated by reference, the active agent is preferably formulated to be locally deliverable to bone proximate the implant in sustained-release or in at least a two-phased release scheme. In the latter, a first phase rapidly releases a first quantity of the active agent, and the second and subsequent phases gradually release a second quantity of the active agent, whereby bone formation stimulated by the active agent is modulated.

Medical devices such as bone implants feature implantable portions bearing a compound or composition of present invention (e.g., a compound or composition of Formula I) foster quicker and more complete bone formation in situ. The implantable portion of the medical device can be desirable at least partially or totally covered or impregnated with a compound or composition of the present invention. In some embodiments, the medical device is externally coated with a compound or composition as described herein. In some embodiments, the external coating completely coats the implantable portion of the structural support. In some embodiments, the structural support (e.g., matrix or scaffold) comprises a compound or composition as described herein within the support, i.e., internally. In some embodiments, the structural support (e.g., matrix or scaffold) comprises an external coating of a compound or composition as described herein and also comprises the compound or composition within the support, i.e., internally.

Medical devices of the present invention include pins, rods, screws, plates, and orthopedic or dental implants. In some embodiments, the medical devices are made from material comprising metal, polymer, or ceramic, or from combinations thereof. Metals useful for making medical devices of the present invention include, but are not limited to cobalt, chrome, chromium, stainless steel, titanium, titanium alloys, tantalum, trabecular metal. Polymers useful for making medical devices of the present invention include, but are not limited to ultra high molecular weight polyethylene or high density polyethylene. In some embodiments, carbon fiber is combined with polyethylene. Additional useful polymers are described below. Ceramics useful for making medical devices of the present invention include, but are not limited to aluminum oxide, calcium phosphates, hydroxyapatite, zirconium oxide, silicon oxide.

In some other embodiments, the implantable portion of the structural support comprises an osteoconductive matrix. The matrix material can be conducive to bone growth. This can be desirable for materials such as teeth and artificial bone graft sections, and the like. Alternatively, when the implantable sections are load bearing and formed, e.g., of stainless steel, these implantable sections can be desirable when formed with a coating of a compound or composition of the present invention. In that event, it is desirable to also provide a separate matrix material conducive to forming new bone growth.

In some embodiments, the matrix comprises particles of porous materials. The pores are preferred to be of a dimension to permit progenitor cell migration into the matrix and subsequent differentiation and proliferation. In some embodiments, the pore size of the matrix is at least 5 µm, e.g., at least 5, 10, 15, 20, 25, 30, 40, 50, 60, 70, 80, 90, 100, 110, 115, 120, 125, 150, 175, 200, 250, 300, 400, 450, 500, 550, 600, 650, 700, 750, 800, 850, 900, 950, 1000, 1250, 1500, 1750 or 2000 µm. In some embodiments, the scaffold or matrix comprises a mesh structure, a foam structure, a sponge structure, or a fiber structure.

A scaffold or matrix for use in a device as described herein can comprise a synthetic and/or biologic material. In some embodiments, the scaffold or matrix comprises a naturally occurring polymer, a synthetic biodegradable polymer, a synthetic nonbiodegradable polymer, a bioceramic, a bioglass, a bioactive glass, a biocompsite, or combinations thereof. Natural and synthetic polymers, bioceramics, and bioglasses for use in scaffolds are known in the art. See, e.g., Dhandayuthapani et al., International Journal of Polymer Science, volume 2011, article ID 290602 (2011), incorporated by reference herein. Natural polymers include, but are not limited to, proteins (e.g., silk, collagen, gelatin, fibrinogen, elastin, keratin, actin, and myosin), polysaccharides (e.g., cellulose, amylose, dextran, chitin, chitosan, and glycosaminoglycans), and polynucleotides (e.g., DNA and RNA). Synthetic polymers include, but are not limited to, PLA, PGA, PLLA, PLGA, PCL, PLDLA, PDS, PGCL, PEA, PCA, PDLLA, PEU, and PBT. Bioceramics and bioglasses include, but are not limited to, HAP, TCP, CP ceramics, BCP, and TCP. In some embodiments, the scaffold or matrix is a hydrogel scaffold, a fibrous scaffold, a microsphere scaffold, a polymer-bioceramic composite scaffold, or an acellular scaffold.

In some embodiments, suitable matrixes include those comprising composite biomaterials having a sponge-like structure such as those containing, e.g., phosphophoryn and/or collagen as taught in Takashi Saito's U.S. Publication No. 2006/0188544, published Aug. 24, 2006, the subject matter of which is hereby incorporated by reference. Such coatings include, for example, the single and multilayer coatings taught in U.S. Publication No. 2006/0204542 to Zongtao Zhang et al, published Sep. 14, 2006, as well as those in U.S. Pat. Nos. 6,949,251, 5,298,852, 5,939,039, and 7,189,263 and can be made by conventional methods including the methods taught therein, the subject matter of which is hereby incorporated by reference.

In some embodiments, the matrix is an osteoconductive matrix. In some embodiments, the osteoconductive matrix includes an osteoinductive agent such as bone allograft, bone autograft, demineralized bone or periodontal ligament cells or combinations thereof. In some other embodiments, the osteoconductive matrix can be a calcium salt, calcium sulfate, biphasic calcium phosphate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a biocompatible ceramic, a calcium phosphate ceramic, polytetrafluoroethylene, sulfate salt, borosilicate, bioactive glass, Mastergraft variant, Vitoss variant, cement hydrogel, or combinations thereof. One of skill in the art will appreciate that other osteoconductive matrices and osteoinductive agents are useful in the present invention.

In some embodiments, the medical devices described herein include both a Compound of Formula I and an additional therapeutic agent. Suitable additional therapeutic agents include the combinations discussed in Section IX. C., above. For example, the medical devices can Include a compound of Formula I in combination with an anabolic agent. In some embodiments, a medical device described herein include a compound of Formula I in combination with a bone morphogenic protein (BMP) or a BMP agonist. In some embodiments, the BMP is selected from the group consisting of BMP2, BMP7, BMP4. In some embodiments, the BMP agonist is a compound described in Vrijens K, et al. PLoS One. 2013; 8(3):e59045, the contents of which is incorporated by reference for all purposes.

XI. Assay for Identification of Compounds for Treating Bone Loss

Compounds useful in the methods of the present invention can be identified via a variety of methods known to one of skill in the art. Several exemplary methods for identifying such antagonists are described herein, including cell-based and in vitro techniques (Journal of Bone and Mineral Research 2006, 21(11), 1738-1749). A general method of identifying compounds involves evaluating the effects of antagonist candidates on bone formation under controlled conditions. Preferably bone formation is determined using Dexa techniques on live animals or uCT on ex vivo samples. Preferred animals include rodents, more preferred are primates. Femur, tibia and vertebrae bones are particularly useful subjects for such study.

Briefly, the test animal is treated with a predetermined dose of a candidate compound. A control animal is treated with a control solution, preferably a non-irritating buffer solution or other carrier. When the candidate compound is delivered in a carrier, the control solution is ideally the carrier absent the candidate compound. Multiple doses of the candidate compound can be applied to the test animal, preferably following a predetermined schedule of dosing. The dosing schedule can be over a period of days, e.g., 1, 2, 3, 4, 5, 6, 7, 8, 9, 10, 15, 20, 25 days or more; over a period of weeks, e.g., 1, 2, 3, 4, 5, 6, 7, 8, 9, 10 weeks or more; or other a period of months, e.g., 1, 2, 3, 4, 5, 6, 7, 8, 9, 10 months or more.

In an exemplary embodiment, localized administration in situ of a candidate compound can be made into a test animal, with a control animal receiving an equal volume of control solution without the candidate compound. Suitable dosage will depend on the nature of the particular candidate compound being tested. By way of example, in dosing it should be noted that systemic administration (e.g., by oral or injection, e.g., intravenously, subcutaneously or intramuscularly), can also be used. Dosing performed by nebulized inhalation, eye drops, or oral ingestion should be at an amount sufficient to produce blood levels of the candidate compound similar to those reached using systemic injection. The amount of candidate compound that can be delivered by nebulized inhalation, eye drops, or oral ingestion to attain these levels is dependent upon the nature of the inhibitor used and can be determined by routine experimentation.

Once the dosing schedule has been completed, both test and control animals are examined to determine the quantity of bone formation present. This can be accomplished by any suitable method, but is preferably performed on live animals to analyze the bone mineral content. Methods for microCT examination of bones in animals are well known in the art. A candidate compound suitable for use in promoting bone formation is identified by noting a significant increase in bone formation in the test animal when compared to the control animal. In some embodiments, a candidate compound is identified as suitable for use in promoting bone formation if the amount of bone formation in the test bone(s) of the test animal is at least 0.5%, 1, 3, 5, 6, 7, 8, 9, 10, 11, 12, 13, 14, 15, 16, 17, 18, 19, 20, 22, 24, 26, 28, 30, 40, 50, 60, 70, 80, 90, 100, 200, 300, 400, 500, 600, 700, 800, 900 or 1000% or more as compared to the comparable bone(s) of the control animal. In some embodiments, bone formation is increased by at least 3%, at least 5%, at least 7%, at least 10%, at least 12%, at least 14%, at least 16%, at least 18%, at least 20%, at least 30%, at least 40%, at least 50% or more as compared to the control animal. Where necessary, levels of bone formation can be calculated by determining the volume of bone formation present in each animal. Calculations can be performed by constructing a 3 dimensional image of the bone formation and calculating the volume from the image with the aid of e.g., histomorphometry.

An example of the molecular modeling system described generally above consists of the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

Compounds may also be identified using a process known as computer, or molecular modeling, which allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user friendly, menu driven interfaces between the molecular design program and the user.

XII. Particular Embodiments of the Present Disclosure

Embodiment 1. A compound according to Formula I.

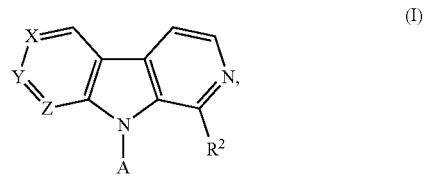

(I)

or a salt, hydrate, prodrug, or isomer thereof, wherein

X is selected from $CR^{3b}$ and N, wherein N is optionally oxidized to the corresponding N-oxide;

Y is selected from $CR^{3'}$ and N, wherein N is optionally oxidized to the corresponding N-oxide;

Z is selected from $CR^{3d}$ and N, wherein N is optionally oxidized to the corresponding N-oxide, provided that at least one of X, Y, and Z is N or the corresponding N-oxide;

A is

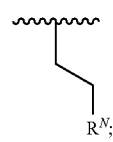

$R^N$ is selected from the group consisting of heterocyclyl and heteroaryl, wherein the heterocyclyl moiety is selected from monocyclic, fused bicyclic, and bridged cyclic, the monocyclic heterocyclyl comprising from 4 to 7 ring members, the fused bicyclic and bridged bicyclic heterocyclyl comprising from 7 to 10 ring members, each heterocyclyl moiety having from 1 to 3 heteroatoms as ring members selected from N, O, and S, wherein each heterocyclyl moiety comprises at least one nitrogen atom as a ring member and is optionally substituted with from 1 to 3 $R^6$ moieties, the heteroaryl moiety comprises from 5 to 10 ring members, wherein at least one ring member is a nitrogen atom and is optionally substituted with from 1 to 3 $R^6$ moieties, each $R^2$, $R^{3b}$, $R^{3c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkyl-OH, —O—$C_{1-6}$ alkyl-OH, $C_{3-6}$ cycloalkyl-$C_{1-4}$alkoxy, and —OH;

R⁶ is selected from the group consisting of —OH, $C_{1-3}$ alkyl, $C_{1-3}$ alkyl-OH, —O—$C_{1-3}$ alkyl, $C_{3-4}$ heteroalkyl, $C_{1-3}$ haloalkyl, —O—$C_{1-3}$ haloalkyl, halogen, and oxo.

Embodiment 2. The compound according to embodiment 1, having the Formula Ia, Ib, Ic, or Id:

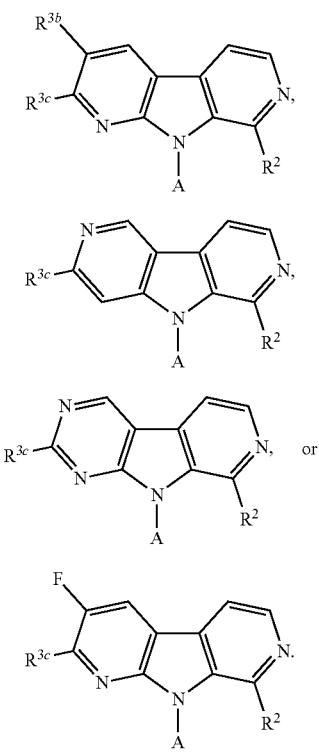

Embodiment 3. The compound of embodiment 1 or 2, wherein R² is selected from the group consisting of H, halogen, $C_{1-6}$ alkyl, $C_{1-6}$ haloalkyl, $C_{1-6}$ alkoxy, and $C_{1-6}$ haloalkoxy.

Embodiment 4. The compound of embodiment 1 or 2, wherein R² is selected from the group consisting of halogen, $C_{1-6}$ alkyl, $C_{1-6}$ haloalkyl, and $C_{1-6}$ alkoxy.

Embodiment 5. The compound of embodiment 4, wherein R² is $C_{1-6}$ alkyl or $C_{1-6}$ haloalkyl.

Embodiment 6. The compound of embodiment 5, wherein R² is $CH_3$ or $CF_3$.

Embodiment 7. The compound of embodiment 6, wherein R² is $CH_3$.

Embodiment 8. The compound of embodiment 6, wherein R² is $CF_3$.

Embodiment 9. The compound of any one of embodiments 1 to 8, wherein
each $R^{3b}$, $R^{3c}$ and $R^{3d}$, when present, is independently selected from the group consisting of H, halogen, $C_{1-6}$ alkyl, $C_{1-6}$ haloalkyl, $C_{1-6}$ alkoxy, $C_{1-6}$ haloalkoxy.

Embodiment 10. The compound of embodiment 9, wherein
each $R^{3b}$, $R^{3c}$ and $R^{3d}$, when present, is independently selected from the group consisting of H, halogen, and $C_{1-6}$ alkoxy.

Embodiment 11. The compound of embodiment 10, wherein
each $R^{3b}$, $R^{3c}$ and $R^{3d}$, when present, is independently selected from the group consisting of H, F, and methoxy.

Embodiment 12. The compound of any one of embodiments 1 to 8, wherein
$R^{3c}$, when present, is methoxy.

Embodiment 13. The compound of any of embodiments 1 to 11, wherein
$R^N$ is heterocyclyl or heteroaryl.

Embodiment 14. The compound of embodiment 13, wherein $R^N$ is heterocyclyl.

Embodiment 15. The compound of embodiment 14, wherein $R^N$ is a monocyclic heterocyclyl.

Embodiment 16. The compound of embodiment 13, wherein $R^N$ is

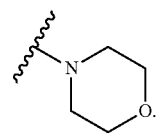 [SMILES: *N1CCOCC1]

Embodiment 17. The compound of embodiment 1, wherein
R² is selected from the group consisting of H, $C_{1-6}$ alkyl, and $C_{1-6}$ haloalkyl,
$R^{3c}$, if present, is H or $C_{1-6}$ alkoxy;
$R^{3b}$ or $R^{3d}$, if present, is H or halogen; and
$R^N$ is heterocyclyl or heteroaryl.

Embodiment 18. The compound of embodiment 17, wherein
R² is H or $C_{1-6}$ haloalkyl;
$R^{3c}$, if present, is $C_{1-6}$ alkoxy;
$R^{3b}$ or $R^{3d}$, if present, is H or halogen; and
$R^N$ is

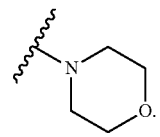 [SMILES: *N1CCOCC1]

Embodiment 19. The compound of embodiment 2, wherein
R² is $C_{1-6}$ alkyl or $C_{1-6}$ haloalkyl;
$R^{3b}$, if present, is H or halogen;
$R^{3c}$ is $C_{1-6}$ alkoxy; and
$R^N$ is heterocyclyl or heteroaryl.

Embodiment 20. The compound of embodiment 19, wherein
R² is $C_{1-6}$ haloalkyl;
$R^{3b}$, if present, is H or halogen;
$R^{3c}$ is $C_{1-6}$ alkoxy; and
$R^N$ is

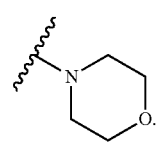

Embodiment 21. The compound of embodiment 20, wherein
R$^2$ is CF$_3$; and
R$^{3c}$ is methoxy.

Embodiment 22. The compound of embodiment 1, selected from the group consisting of

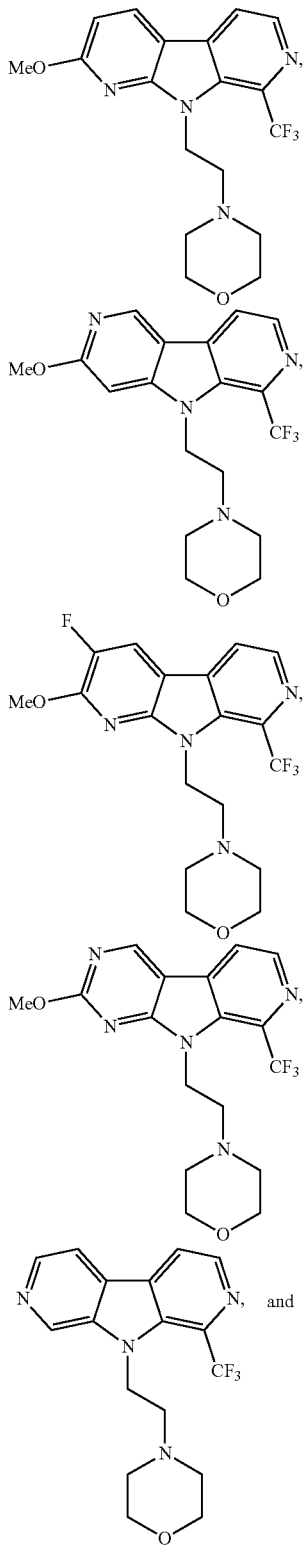

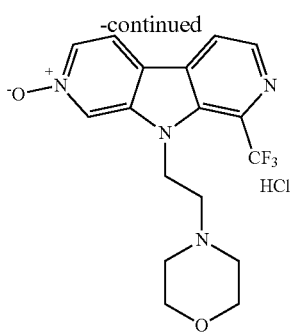

or salts, hydrates, or prodrugs thereof.

Embodiment 23. A formate salt of a compound of any one of embodiments 1 to 22.

Embodiment 24. A sulfate salt of a compound of any of embodiments 1 to 22.

Embodiment 25. A citrate salt of a compound of any one of embodiments 1 to 22.

Embodiment 26. A hydrochloride salt of a compound of any one of embodiments 1 to 22.

Embodiment 27. A prodrug of a compound of any one of embodiments 1 to 22.

Embodiment 28. A pharmaceutical composition comprising a compound of any of embodiments 1 to 27 and a pharmaceutically acceptable excipient.

Embodiment 29. A method of promoting bone formation a subject in need thereof, comprising administering to the subject a therapeutically effective of a compound of any one of embodiments 1 to 28, thereby promoting bone formation in the subject.

Embodiment 30. The method of embodiment 29, wherein the bone formation is promoted at a surgical site of injury or localized condition.

Embodiment 31. The method of embodiment 30, wherein the bone formation is promoted at a surgical site selected from the group consisting of a bone fracture and weakened bone.

Embodiment 32. The method of embodiment 30, wherein the subject is in need of a spinal fusion, arthrodesis or an orthopedic or periodontal synthetic bone graft or implant.

Embodiment 33. The method of embodiment 29, wherein the bone formation is systemic.

Embodiment 34. The method of any of embodiments 29-33, wherein the subject has a low bone mass/density condition, a bone fracture, or periodontal disease.

Embodiment 35. The method of embodiment 34, wherein the low bone mass condition is selected from osteoporosis, osteopenia, osteogenesis imperfecta (OI), osteoporosis-pseudoglioma syndrome (OPPG), and secondary low bone condition.

Embodiment 36. The method of embodiment 35, wherein the low bone mass condition is selected from the group consisting of osteoporosis, osteopenia, and osteoporosis-pseudoglioma syndrome (OPPG).

Embodiment 37. The method of any of embodiments 29-36, further comprising administering to the subject an osteoconductive matrix.

Embodiment 38. The method of embodiment 37, wherein the osteoconductive matrix comprises an osteoinductive agent selected from the group consisting of bone allograft, bone autograft, and periodontal ligament cells.

Embodiment 39. The method of embodiment 37, wherein the osteoconductive matrix comprises a calcium salt, calcium sulfate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a biocompatible ceramic, a calcium phosphate ceramic, demineralized bone matrix, biphasic calcium phosphate, biocomposite, tantalum, titanium, polytetrafluoroethylene, sulfate salt, hydrogel, bioglass, or combinations thereof.

Embodiment 40. The method of embodiment 37, wherein the osteoconductive matrix comprises a calcium salt, calcium sulfate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a biocompatible ceramic, a calcium phosphate ceramic, demineralized bone matrix, biphasic calcium phosphate, biocomposite, tantalum, titanium, polytetrafluoroethylene, sulfate salt, or hydrogel.

Embodiment 41. The method of any of embodiments 29-40, wherein the compound is administered sequentially or in combination with an antiresorptive drug.

Embodiment 42. The method of embodiment 41, wherein the compound is administered to a patient who is being treated with the antiresorptive drug or has previously been treated with the antiresorptive drug.

Embodiment 43. The method of embodiment 41, wherein the antiresorptive drug is selected from the group consisting of denosumab, prolia, a RankL inhibitor, a bisphosphonate, a selective estrogen receptor modulator (SERM), calcitonin, a calcitonin analog, Vitamin D, a Vitamin D analog, and a cathepsin K inhibitor.

Embodiment 44. The method of embodiment 41, wherein the antiresorptive drug is denosumab.

Embodiment 45. The method of embodiment 41, wherein the antiresorptive drug is administered systemically.

Embodiment 46. The method of embodiment 41, wherein the antiresorptive drug is administered locally.

Embodiment 47. The method of any of embodiments 29-46, further comprising administering an anabolic agent.

Embodiment 48. A medical device comprising a structural support, wherein an implantable portion of the structural support is adapted to be permanently implanted within a subject, wherein the implantable portion is attached to a bone, the structural support bearing at least a partial external coating comprising a compound of any one of embodiments 1 to 28.

Embodiment 49. A method of treating bone loss in a subject in need thereof, comprising administering to the subject a therapeutically effective of a compound of any one of embodiments 1 to 28 in series or in combination with an antiresorptive agent, thereby treating bone loss in a subject XIII. Examples Example 1: 4-(2-(1-(Trifluoromethyl)-9H-pyrrolo[2,3-c:5,4-c']dipyridin-9-yl)ethyl)morpholine hydrochloride salt

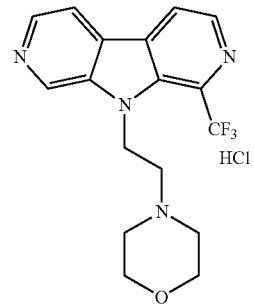 [SMILES: FC(F)(F)c1nccc2c3ccncc3n(CCN3CCOCC3)c12 ; Cl]

A round-bottom flask was charged with 3-bromo-2-trifluoromethylpyridine (500 mg, 2.21 mmol) and 3-amino-4-chloropyridine (298 mg, 2.32 mmol). The flask was flushed with Ar, and PhMe (5 mL) was added. To the resulting solution were added $Cs_2CO_3$ (866 mg, 2.65 mmol), X-Phos (80 mg, 0.16 mmol), and $Pd(OAc)_2$ (25 mg, 0.11 mmol), in that order. The flask was equipped with a Liebig condenser and the mixture was degassed and stirred overnight at 110° C. under Ar. The mixture was allowed to cool, diluted with EtOAc, and washed once with water, once with brine, dried ($MgSO_4$), and evaporated. Flash chromatography over $SiO_2$ (40 g) using 30-100% EtOAc-hexanes (gradient elution) afforded 4-chloro-N-(2-(trifluoromethyl)pyridin-3-yl)pyridin-3-amine (314 mg, 52%).

A flask was charged with 4-chloro-N-(2-(trifluoromethyl)pyridin-3-yl)pyridin-3-amine (314 mg, 1.15 mmol) and DMA (10 mL) was added, followed by $K_2CO_3$ (317 mg, 2.30 mmol). The mixture was then degassed and placed under Ar atmosphere. $t-Bu_3P$—$HBF_4$ (85 mg, 0.30 mmol) followed by $Pd(OAc)_2$ (26 mg, 0.12 mmol) were added, the mixture was degassed again, placed under Ar, and heated at 130° C. overnight. The mixture was then re-charged with additional portions of $t-Bu_3P$—$HBF_4$ (85 mg, 0.30 mmol) and $Pd(OAc)_2$ (26 mg, 0.12 mmol), and stirred at 130° C. overnight again. The mixture was allowed to cool, diluted with EtOAc, washed once with water, once with brine, dried ($MgSO_4$), and evaporated. Flash chromatography over $SiO_2$ (24 g) using 60-100% EtOAc-hexanes afforded 1-(trifluoromethyl)-9H-pyrrolo[2,3-c:5,4-c']dipyridine (100 mg, 37%).

4-(2-chloroethyl)morpholine HCl (94.1 mg, 0.510 mmol) was added to a stirred solution of 1-(trifluoromethyl)-9H-pyrrolo[2,3-c:5,4-c']dipyridine (100 mg, 0.420 mmol) in DMF (5 mL). NaH (60% in oil, 100 mg, 2.52 mmol) was added in one portion, the flask was flushed with Ar, and the mixture was heated at 60° C. overnight with stirring. The mixture was allowed to cool to room temperature, diluted with EtOAc, washed once with water, once with brine, dried ($MgSO_4$), and evaporated. Flash chromatography of the residue over $SiO_2$ (12 g) using 50-100% EtOAc-hexanes, followed by 50% MeOH-EtOAc, afforded compound 4-(2-(1-(trifluoromethyl)-9H-pyrrolo[2,3-c:5,4-c']dipyridin-9-yl)ethyl)morpholine (14 mg, 10%) and oxidized compound 9-(2-morpholinoethyl)-8-(trifluoromethyl)-9H-pyrrolo[2,3-c:5,4-c']dipyridine 2-oxide (10 mg, 6%).

Characterization for 4-(2-(1-(trifluoromethyl)-9H-pyrrolo[2,3-c:5,4-c']dipyridin-9-yl)ethyl)morpholine: $^1$H NMR (CDCl$_3$, 400 MHz) δ 9.16 (s, 1H), 8.63 (d, 1H, J=5.2 Hz), 8.59 (d, 1H, J=4.8 Hz), 8.25 (d, 1H, J=5.2 Hz), 8.04 (dd, 1H, J=5.2, 0.8 Hz), 4.74 (t, 2H, J=7.6 Hz), 3.69 (t, 4H, J=4.8 Hz), 2.79 (t, 2H, J=7.6 Hz), 2.54 (t, 4H, J=4.8 Hz).

HCl (2 M in Et$_2$O, 10 eq) was added via syringe to a stirred solution of 4-(2-(1-(trifluoromethyl)-9H-pyrrolo[2,3-c:5,4-c']dipyridin-9-yl)ethyl)morpholine or oxidized compound 9-(2-morpholinoethyl)-8-(trifluoromethyl)-9H-pyrrolo[2,3-c:5,4-c']dipyridine 2-oxide in CH$_2$Cl$_2$ (1 mL). Stirring was continued for 5 min and then the volatiles were removed in-vacuo. The residue was purified by trituration using 80% CH$_2$Cl$_2$-hexanes to afford 4-(2-(1-(trifluoromethyl)-9H-pyrrolo[2,3-c:5,4-c']dipyridin-9-yl)ethyl)morpholine hydrochloride salt or oxidized compound 9-(2-morpholinoethyl)-8-(trifluoromethyl)-9H-pyrrolo[2,3-c:5,4-c']dipyridine 2-oxide hydrochloride salt in quantitative yield.

Characterization for 4-(2-(1-(trifluoromethyl)-9H-pyrrolo[2,3-c:5,4-c']dipyridin-9-yl)ethyl)morpholine hydrochloride salt: $^1$H NMR (DMSO-d$_6$, 400 MHz) δ 12.00 (s, 1H), 9.88 (s, 1H), 8.88 (d, 1H, J=4.8 Hz), 8.80 (s, 2H), 8.74 (d, 1H, J=4.8 Hz), 5.15 (t, 2H, J=8.4 Hz), 4.04 (m, 2H), 3.86 (m, 2H), 3.59 (m, 2H), 3.50 (m, 2H), 3.23 (m, 2H). LCMS m/z 351.2 ([M+H]$^+$, C$_{17}$H$_{18}$F$_3$N$_4$O requires 351.2).

Example 2: 9-(2-Morpholinoethyl)-8-(trifluoromethyl)-9H-pyrrolo[2,3-c:5,4-c']dipyridine 2-oxide hydrochloride salt

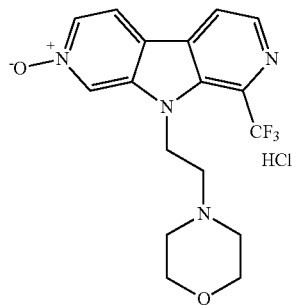

Free base: $^1$H NMR (CDCl$_3$, 400 MHz) δ 9.94 (s, 1H), 8.54 (d, 1H, J=5.2 Hz), 8.03 (d, 1H, J=5.2 Hz), 7.24 (d, 1H, J=7.2 Hz), 6.93 (d, 1H, J=7.2 Hz), 4.27 (t, 2H, J=6.4 Hz), 3.68 (t, 4H, J=4.4 Hz), 2.78 (t, 2H, J=6.4 Hz), 2.54 (t, 4H, J=4.4 Hz).

HCl Salt: $^1$H NMR (DMSO-d$_6$, 400 MHz) δ 12.84 (s, 1H), 10.24 (bs, 1H), 8.48 (d, 1H, J=5.2 Hz), 8.43 (d, 1H, J=5.2 Hz), 7.59 (d, 1H, J=7.2 Hz), 7.28 (d, 1H, J=7.2 Hz), 4.51 (m, 2H), 3.99 (m, 2H), 3.62 (m, 6H), 3.17 (m, 2H). LCMS m/z 367.2 ([M+H]$^+$, C$_{17}$H$_{18}$F$_3$N$_4$O$_2$ requires 367.2).

Example 3: 4-(2-(2-Methoxy-8-(trifluoromethyl)-9H-pyrrolo[2,3-b:5,4-c']dipyridin-9-yl)ethyl)morpholine hydrochloride salt

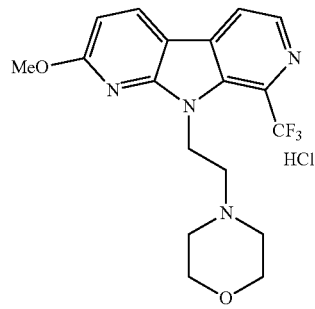 [SMILES: COc1ccc2c3ccnc(C(F)(F)F)c3n(CCN3CCOCC3)c2n1 ; Cl]

To a 0° C. solution of 6-methoxypyridin-2-amine (5.0 g, 40 mmol) in CHCl$_3$ (150 ml) was added portionwise NCS (5.35 g, 40 mmol). The reaction solution was stirred at room temperature for 3 days and then diluted with CH$_2$Cl$_2$, washed with water, NaHCO$_3$ (sat), brine, dried over MgSO$_4$ and concentrated. Product was purified by silica chromatography using a 90% hexanes/10% EtOAc to 50% hexanes/50% EtOAc gradient to give 3-chloro-6-methoxypyridin-2-amine (4.8 g, 75%).

To a dry tube was added 3-bromo-2-trifluoromethylpyridine (500 mg, 2.2 mmol), cesium carbonate (866 mg, 2.7 mmol), X-Phos (80 mg, 0.16 mmol), Pd(OAc)$_2$ (25 mg, 0.1 mmol) and 3-chloro-6-methoxypyridin-2-amine (370 mg, 2.3 mmol). The reaction solution was diluted with toluene (5 ml), degassed and stirred at 120° C. overnight and then cooled to room temperature, diluted with EtOAc, washed with water, brine, dried over MgSO$_4$ and concentrated. Product was purified by silica chromatography using a 80% Hexanes/20% EtOAc to 100% EtOAc gradient to give 3-chloro-6-methoxy-N-(2-(trifluoromethyl)pyridin-3-yl)pyridin-2-amine (588 mg, 88%).

To a dry tube was added the 3-chloro-6-methoxy-N-(2-(trifluoromethyl)pyridin-3-yl)pyridin-2-amine (588 mg, 1.9 mmol), potassium carbonate (536 mg, 3.9 mmol) and DMA (20 ml). The reaction was degassed and (t-Bu$_3$)PHBF$_4$ (113 mg, 0.39 mmol) and Pd(OAc)$_2$ (45 mg, 0.19 mmol) were introduced. The reaction was stirred at 120° C. overnight. An additional aliquot of catalyst was added and the reaction stirred at 120° C. overnight then cooled to room temperature, diluted with EtOAc, washed with water, brine, dried over MgSO$_4$ and concentrated. The product was purified by silica chromatography using a 85% hexanes/15% EtOAc to 50% hexanes/50% EtOAc gradient. The product was repurified by reverse phase chromatography on C$_{18}$ column using a 50% ACN/50% water (0.1% FA) to 90% ACN/10% water (0.1% FA) gradient. As the Des-chloro material was still present, the product was again repurified by HPLC C$_{18}$ column using a 10% ACN/90% water (0.1% FA) to 90% ACN/10% water (0.1% FA) gradient to give 2-methoxy-8-(trifluoromethyl)-9H-pyrrolo[2,3-b:5,4-c']dipyridine (47 mg, 9%).

Characterization for 2-methoxy-8-(trifluoromethyl)-9H-pyrrolo[2,3-b:5,4-c']dipyridine: $^1$H NMR (CDCl$_3$, 400 MHz) δ 8.47 (d, 1H, J=4.8 Hz), 8.23 (dd, 1H, J=8.4, 0.8 Hz), 7.98 (d, 1H, J=4.8 Hz), 6.74 (dd, 1H, J=8.4, 0.8 Hz), 4.76 (t, 2H, J=7.6 Hz), 4.07 (s, 3H), 3.69 (t, 4H, J=4.8 Hz), 2.77 (t, 2H, J=7.6 Hz), 2.60 (t, 4H, J=4.4 Hz).

To a solution of 2-methoxy-8-(trifluoromethyl)-9H-pyrrolo[2,3-b:5,4-c']dipyridine (47 mg, 0.18 mmol) in DMF (3 ml) was added 4-(2-chloroethyl)morpholine hydrochloride (66 mg, 0.35 mmol) followed by sodium hydride (60% in oil, 42 mg, 1.1 mmol). The solution was stirred at 60° C. for overnight then cooled to room temperature, quenched with NaHCO$_3$ (sat) and diluted with EtOAc. The crude product was washed with NaHCO$_3$ (sat), brine, dried over MgSO$_4$ and concentrated. The product was purified by silica chromatography using a 70% hexanes/30% EtOAc to 100% EtOAc gradient to give 4-(2-(2-Methoxy-8-(trifluoromethyl)-9H-pyrrolo[2,3-b:5,4-c']dipyridin-9-yl)ethyl)morpholine (42 mg, 63%). This product was then diluted with CH$_2$Cl$_2$ and 1 ml of 4M HCl in dioxane was added and stirred 10 min then evaporated to dryness. Trituration from CH$_2$Cl$_2$/hexanes gave the 4-(2-(2-Methoxy-8-(trifluoromethyl)-9H-pyrrolo[2,3-b:5,4-c']dipyridin-9-yl)ethyl)morpholine hydrochloride salt in quantitative yield.

Characterization for 4-(2-(2-Methoxy-8-(trifluoromethyl)-9H-pyrrolo[2,3-b:5,4-c']dipyridin-9-yl)ethyl)morpholine hydrochloride salt: $^1$H NMR (DMSO-d$_6$, 400 MHz) δ 11.54 (s, 1H), 8.69 (d, 1H, J=8.4 Hz), 8.53 (d, 1H, J=5.2 Hz), 8.46 (d, 1H, J=4.8 Hz), 6.91 (d, 1H, J=8.4 Hz), 4.98 (m, 2H), 4.09 (s, 3H), 4.02 (d, 2H, J=12.4 Hz), 3.84 (m, 2H), 3.65 (d, 2H, J=10.4 Hz), 3.45 (m, 2H), 3.22 (m, 2H). LCMS m/z 381.2 ([M+H]$^+$, C$_{18}$H$_{20}$F$_3$N$_4$O$_2$ requires 381.2).

Example 4: 4-(2-(3-Methoxy-6-(trifluoromethyl)-5H-pyrrolo[2,3-c:4,5-c']dipyridin-5-yl)ethyl)morpholine hydrochloride salt

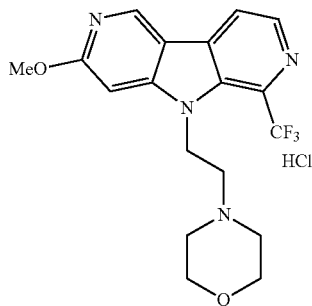 [SMILES: COc1cc2c(cn1)c1ccnc(C(F)(F)F)c1n2CCN1CCOCC1 ; Cl]

A flask was charged with 5-chloro-2-methoxypyridin-4-amine HCl salt (0.6065 g, 3.109 mmol), 3-bromo-2-trifluoromethylpyridine (3) (0.77 g, 3.41 mmol), Cs$_2$CO$_3$ (2.53 g, 7.77 mmol), X-Phos ligand (0.22 g, 0.46 mmol), and Pd(OAc)$_2$ (0.14 g, 0.62 mmol). The flask was equipped with a condenser, flushed with Ar, and m-xylene (8.8 mL) was added. The mixture was degassed, placed under Ar, and refluxed overnight with stirring. The mixture was allowed to cool and, diluted with water and EtOAc, and filtered through Celite (using EtOAc to wash the filter-cake). The aqueous layer was extracted once with EtOAc, and the combined organic extracts were washed once with water, once with brine, dried (Na$_2$SO$_4$), and evaporated. Purification of the residue by flash chromatography gave impure material (as an inseparable mixture of starting aniline and the desired product). The mixture was separated by flash chromatography over reverse phase C-18 silica, using Biotage SNAP cartridge KP-C18-HS (60 g) and eluting with 30-95% MeCN—H$_2$O (gradient elution), to afford N-(5-chloro-2-methoxypyridin-4-yl)-2-(trifluoromethyl)pyridin-3-amine (0.3069 g, 33%).

A microwave flask was charged with t-Bu$_3$P—HBF$_4$ (59 mg, 0.20 mmol), K$_2$CO$_3$ (0.35 g, 2.5 mmol), Pd(OAc)$_2$ (34 mg, 0.15 mmol), and PivOH (21 mg, 0.20 mmol). The flask was capped, flushed with Ar, and N-(5-chloro-2-methoxypyridin-4-yl)-2-(trifluoromethyl)pyridin-3-amine (0.3069 g, 1.011 mmol) in DMA (4 mL) was added via syringe. Ar was bubbled through the solution for 5 min, with stirring, before heating in the microwave at 164° C. for 2 h, with stirring. The mixture was allowed to cool, diluted with EtOAc, and filtered through Celite, using EtOAc to wash the filter-cake. The mixture was then washed twice with brine, dried (Na$_2$SO$_4$), and evaporated. Purification of the residue by flash chromatography over SiO$_2$ (40 g) using 5-40% EtOAc-hexanes (gradient elution) afforded 2-methoxy-8-(trifluoromethyl)-9H-pyrrolo[2,3-b:5,4-c']dipyridine (34.2 mg, 13%).

NaH (60% in oil, 30 mg, 0.75 mmol) was added in one portion to a stirred solution of 2-methoxy-8-(trifluoromethyl)-9H-pyrrolo[2,3-b: 5,4-c']dipyridine (34 mg, 0.127 mmol), 4-(2-chloroethyl)morpholine hydrochloride (48 mg, 0.25 mmol), and TBAI (5 mg, 0.01 mmol) in DMF (1.8 mL). The flask was flushed with N$_2$ and heated at 60° C. overnight with stirring. The next day the mixture was allowed to cool to room temperature, diluted with EtOAc, washed once with water, once with brine, dried (Na$_2$SO$_4$), and evaporated. Purification of the residue by flash chromatography over SiO$_2$ (12 g) using 20-100% EtOAc-hexanes (gradient elution) afforded 4-(2-(3-methoxy-6-(trifluoromethyl)-5H-pyrrolo[2,3-c:4,5-c']dipyridin-5-yl)ethyl)morpholine (33 mg, 69%).

Characterization for 4-(2-(3-methoxy-6-(trifluoromethyl)-5H-pyrrolo[2,3-c:4,5-c']dipyridin-5-yl)ethyl)morpholine: $^1$H NMR (CDCl$_3$, 400 MHz) δ 8.98 (s, 1H), 8.53 (d, 1H, J=5.2 Hz), 8.11 (d, 1H, J=5.2 Hz), 6.79 (s, 1H), 4.52 (t, 2H, J=7.6 Hz), 4.07 (s, 3H), 3.72 (t, 4H, J=4.4 Hz), 2.72 (t, 2H, J=7.6 Hz), 2.56 (t, 4H, J=4.4 Hz).

HCl (0.2 M in Et$_2$O, 0.42 mL, 0.084 mmol) was added via syringe to a stirred solution of 4-(2-(3-methoxy-6-(trifluoromethyl)-5H-pyrrolo[2,3-c:4,5-c']dipyridin-5-yl)ethyl)morpholine (16 mg, 0.042 mmol) in CH$_2$Cl$_2$ (1 mL). The mixture was stirred for 10 min and the volatiles were removed in-vacuo to obtain an off-white solid. The solid was triturated with 1:1 Et$_2$O-hexanes (ca. 2 mL) to afford 4-(2-(3-methoxy-6-(trifluoromethyl)-5H-pyrrolo[2,3-c:4,5-c'] dipyridin-5-yl)ethyl)morpholine hydrochloride salt (17.5 mg, quantitative) as a white solid.

Characterization for 4-(2-(3-methoxy-6-(trifluoromethyl)-5H-pyrrolo[2,3-c:4,5-c']dipyridin-5-yl)ethyl)morpholine hydrochloride salt: $^1$H NMR (DMSO-d$_6$, 400 MHz) δ 11.83 (s, 1H), 9.27 (s, 1H), 8.58 (d, 1H, J=5.2 Hz), 8.55 (d, 1H, J=4.8 Hz), 7.43 (s, 1H), 4.88 (t, 2H, J=8.4 Hz), 4.01 (s, 3H), 3.82 (d, 2H, J=11.6 Hz), 3.70 (m, 2H), 3.59 (d, 2H, J=11.2 Hz), 3.35 (m, 2H), 3.18 (m, 2H). LCMS m/z 381.2 ([M+H]$^+$, C$_{18}$H$_{20}$F$_3$N$_4$O$_2$ requires 381.2).

Example 5: 4-(2-(2-Methoxy-8-(trifluoromethyl)-9H-pyrido[4',3':4,5]pyrrolo[2,3-d]pyrimidin-9-yl)ethyl)morpholine

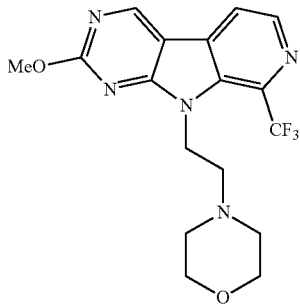 [SMILES: COc1ncc2c3ccnc(C(F)(F)F)c3n(CCN3CCOCC3)c2n1]

MeONa (25% in MeOH, 3.3 mL, 14.6 mmol) was added to a stirred solution of 2,5-dichloropyrimidin-4-amine (2 g, 12.2 mmol) in methanol (40 mL). The mixture was stirred at 50° C. for 4 h with protection from moisture. The mixture was then allowed to cool to room temperature and quenched by addition of saturated $NH_4Cl_{(aq)}$. EtOAc was added and the organic was washed once with $NaHCO_{3(aq)}$, once with brine, and dried ($MgSO_4$). Evaporation of the solvent provided 6-amino-5-chloro-2-methoxypyrimidine without further purification.

A microwave flask was charged with 6-amino-5-chloro-2-methoxypyrimidine (404 mg, 2.53 mmol) and 3-bromo-2-trifluoromethylpyridine (500 mg, 2.21 mmol). The flask was flushed with Ar and DMF (3 mL) was added via syringe. $Cs_2CO_3$ (866 mg, 2.66 mmol) followed by X-Phos ligand (80 mg, 0.16 mmol) were added. The solution was degassed, then Pd(OAc)$_2$ (25 mg, 0.11 mmol) was added and the flask was re-flushed with Ar. The mixture was heated at 160° C. in the microwave (Biotage) for 2 h, allowed to cool, and then diluted with EtOAc, washed once with water, once with brine, and dried ($MgSO_4$). Flash chromatography over $SiO_2$ (40 g) using 20-80% EtOAc-hexanes (gradient elution) afforded 5-chloro-2-methoxy-N-(2-(trifluoromethyl)pyridin-3-yl)pyrimidin-4-amine (120 mg, 18%).

A microwave flask was charged with 5-chloro-2-methoxy-N-(2-(trifluoromethyl)pyridin-3-yl)pyrimidin-4-amine (120 mg, 0.394 mmol) and DMA (5 mL) was added, followed by $K_2CO_3$ (109 mg, 0.788 mmol). The mixture was then degassed and placed under Ar atmosphere. t-Bu$_3$P—HBF$_4$ (22.8 mg, 0.0788 mmol) followed by Pd(OAc)$_2$ (8.8 mg, 0.0394 mmol) were added, the mixture was degassed again, placed under Ar, and heated at 130° C. overnight. At this point the conversion was low (LCMS) and so the mixture was re-charged with additional portions of t-Bu$_3$P—HBF$_4$ ligand (22.8 mg, 0.0788 mmol) and Pd(OAc)$_2$ catalyst (8.8 mg, 0.0394 mmol) and heated in the microwave (Biotage) at 160° C. for 1.5 h. At this point the conversion was ca. 50% (LCMS) and the mixture was re-charged with additional portions of t-Bu$_3$P—HBF$_4$ ligand (22.8 mg, 0.0788 mmol) and Pd(OAc)$_2$ catalyst (8.8 mg, 0.0394 mmol) and heated in the microwave (Biotage) at 160° C. for 2 h. The mixture was allowed to cool, diluted with EtOAc, and washed once with saturated $NaHCO_{3(aq)}$, once with brine, and dried ($MgSO_4$). Flash chromatography over $SiO_2$ (24 g) using 20-80% EtOAc-hexanes (gradient elution) afforded 2-methoxy-8-(trifluoromethyl)-9H-pyrido[4',3':4,5]pyrrolo[2,3-d]pyrimidine (34 mg, 33%).

4-(2-Chloroethyl)morpholine (0.01 mL, 0.05 mmol), followed by Tsunoda's reagent ((cyanomethylene)tributylphosphorane, 15 mg, 0.05 mmol) were added via syringe to a stirred solution of 2-methoxy-8-(trifluoromethyl)-9H-pyrido[4',3':4,5]pyrrolo[2,3-d]pyrimidine (7 mg, 0.03 mmol) in PhMe (0.8 mL) under $N_2$. The mixture was heated at 100° C. overnight with stirring, allowed to cool, and diluted with EtOAc. The mixture was washed once with water, once with brine, and dried ($Na_2SO_4$). Evaporation of the solvent and flash chromatography over $SiO_2$ (0.5×10 cm) in a Pasteur pipette using 60-100% EtOAc-hexanes afforded 4-(2-(2-Methoxy-8-(trifluoromethyl)-9H-pyrido[4',3':4,5]pyrrolo[2,3-d]pyrimidin-9-yl)ethyl)morpholine (2.8 mg, 28%).

Characterization for 4-(2-(2-Methoxy-8-(trifluoromethyl)-9H-pyrido[4',3':4,5]pyrrolo[2,3-d]pyrimidin-9-yl)ethyl)morpholine $^1$H NMR (CDCl$_3$, 400 MHz) δ 9.19 (s, 1H), 8.61 (d, 1H, J=4.8 Hz), 8.10 (d, 1H, J=5.2 Hz), 4.74 (t, 2H, J=7.6 Hz), 4.15 (s, 3H), 3.63 (t, 4H, J=4.8 Hz), 2.75 (t, 2H, J=7.6 Hz), 2.57 (t, 4H, J=4.4 Hz). LCMS m/z 382.2 ([M+H]$^+$, $C_{17}H_{19}F_3N_5O_2$ requires 382.2).

Example 6: 4-(2-(3-Fluoro-2-methoxy-8-(trifluoromethyl)-9H-pyrrolo[2,3-b:5,4-c']dipyridin-9-yl)ethyl)morpholine hydrochloride salt

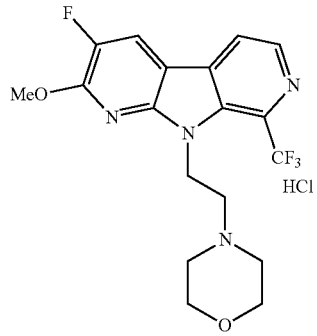 [SMILES: COc1nc2c(cc1F)c1ccnc(C(F)(F)F)c1n2CCN1CCOCC1 ; Cl]

Selectfluor (192 mg, 0.542 mmol) was added, in one portion, to a stirred solution of 2-methoxy-8-(trifluoromethyl)-9H-pyrrolo[2,3-b: 5,4-c']dipyridine (96.6 mg, 0.362 mmol) in MeCN (3 mL). The flask was flushed with $N_2$ and heated to 65 C, with stirring, for 2 days. The mixture was then diluted with EtOAc and washed once with dilute $NaCl_{(aq)}$, once with brine, dried ($Na_2SO_4$), and evaporated. The residue was filtered through a plug of $SiO_2$ (2×4 cm), using 30% EtOAc-hexanes, to afford a mixture of 2-methoxy-8-(trifluoromethyl)-9H-pyrrolo[2,3-b:5,4-c']dipyridine/3-fluoro-2-methoxy-8-(trifluoromethyl)-9H-pyrrolo[2,3-b:5,4-c']dipyridine (1:2, 75 mg, 48% based on conversion). The 2-methoxy-8-(trifluoromethyl)-9H-pyrrolo[2,3-b:5,4-c']dipyridine/3-fluoro-2-methoxy-8-(trifluoromethyl)-9H-pyrrolo[2,3-b:5,4-c']dipyridine (1:2) mixture was purified by reverse-phase HPLC (Puri-Flash system, using Phenomenex Synergi 10u MAX-RP 80A 50×50 mm 10 micron column and 10-95% MeCN-water containing 0.1% formic acid gradient elution) to afford a 2-methoxy-8-(trifluoromethyl)-9H-pyrrolo[2,3-b:5,4-c']dipyridine/3-fluoro-2-methoxy-8-(trifluoromethyl)-9H-pyrrolo[2,3-b:5,4-c']dipyridine (3:17) mixture (19.1 mg), which was used in the next step, and another fraction consisting of a 2-methoxy-8-(trifluoromethyl)-9H-pyrrolo[2,3-b:5,4-c']dipyridine/3-fluoro-2-methoxy-8-(trifluoromethyl)-9H-pyrrolo[2,3-b:5,4-c]dipyridine (7:3) mixture (10.4 mg).

A flask was charged 2-methoxy-8-(trifluoromethyl)-9H-pyrrolo[2,3-b:5,4-c']dipyridine/3-fluoro-2-methoxy-8-(trifluoromethyl)-9H-pyrrolo[2,3-b:5,4-c']dipyridine (3:17) mixture (19 mg, 0.066 mmol) from the above experiment, 4-(2-chloroethyl)morpholine hydrochloride salt (25 mg, 0.13 mmol), and TBAI (5 mg, 0.01 mmol). The flask was flushed with $N_2$, and DMF was introduced via syringe, with stirring. NaH (60% oil dispersion, 16 mg, 0.40 mmol) was added and stirring was continued under a stream of $N_2$ for 5 min before the $N_2$ exit needle was removed, and the mixture was heated to 60° C., with stirring, overnight. The next day, the mixture was diluted with EtOAc and washed twice with water, once with brine, dried ($Na_2SO_4$), and evaporated. The residue was crystallized from $CH_2Cl_2$-hexanes to afford partially pure 4-(2-(3-Fluoro-2-methoxy-8-(trifluoromethyl)-9H-pyrrolo[2,3-b:5,4-c']dipyridin-9-yl)ethyl)morpholine (12 mg). The mixture was further purified using silica chromatography using 30-80% EtOAc-hexanes and then crystallized again from $CH_2Cl_2$-hexanes to afford compound 4-(2-(3-fluoro-2-methoxy-8-(trifluoromethyl)-9H-pyrrolo[2,3-b:5,4-c']dipyridin-9-yl)ethyl)morpholine (9 mg).

Characterization for 4-(2-(3-fluoro-2-methoxy-8-(trifluoromethyl)-9H-pyrrolo[2,3-b:5,4-c']dipyridin-9-yl)ethyl)morpholine: $^1$H NMR (CDCl$_3$, 400 MHz) δ 8.49 (d, 1H, J=5.2 Hz), 8.01 (d, 1H, J=9.6 Hz), 7.97 (d, 1H, J=5.2 Hz), 4.76 (t, 2H, J=7.6 Hz), 4.18 (s, 3H), 3.69 (t, 4H, J=4.4 Hz), 2.76 (t, 2H, J=7.6 Hz), 2.60 (t, 4H, J=4.4 Hz).

HCl (0.2 M in $Et_2O$, 0.22 mL, 0.044 mmol) was added via syringe, at a fast drop-wise rate, to a stirred solution of 4-(2-(3-fluoro-2-methoxy-8-(trifluoromethyl)-9H-pyrrolo[2,3-b:5,4-c']dipyridin-9-yl)ethyl)morpholine (9 mg) in $CH_2Cl_2$ (0.8 mL). After stirring for 5 min at room temperature, the volatiles were removed in-vacuo and the resulting solid was washed once with a small volume of 1:1 $Et_2O$-hexanes, to remove grease. The salt was then suspended in water (ca. 2 mL), with the aid of sonication, frozen, and lyophilized to afford 4-(2-(3-fluoro-2-methoxy-8-(trifluoromethyl)-9H-pyrrolo[2,3-b:5,4-c']dipyridin-9-yl)ethyl)morpholine hydrochloride salt (9 mg, quantitative).

Characterization for 4-(2-(3-fluoro-2-methoxy-8-(trifluoromethyl)-9H-pyrrolo[2,3-b:5,4-c']dipyridin-9-yl)ethyl)morpholine hydrochloride salt: $^1$H NMR (DMSO-d$_6$, 400 MHz) δ 11.04 (s, 1H), 8.76 (d, 1H, J=10.4 Hz), 8.54 (d, 1H, J=5.2 Hz), 8.44 (d, 1H, J=4.8 Hz), 4.95 (m, 2H), 4.19 (s, 3H), 4.03 (d, 2H, J=10.8 Hz), 3.79 (m, 2H), 3.65 (d, 2H, J=10.4 Hz), 3.48 (m, 2H), 3.24 (m, 2H). LCMS m/z 399.2 ([M+H]$^+$, $C_{18}H_{19}F_4N_4O_2$ requires 399.2).

Example 7: Modulation of Sclerostin/Wnt Activity

Compounds synthesized in accordance with the methods of Examples 1-6 were assayed for their ability to restore Wnt signaling in the presence of sclerostin consistent with a known sclerostin antagonist, sclerostin Mab. See, Ellies et al., J Bone Miner Res 21:1738-1749 (2006). As shown in Table 1 below, sclerostin antagonized Wnt3a signaling in human embryonic cells. The addition of a known sclerostin antagonist inhibited sclerostin inhibition of Wnt3a signaling, thus restoring Wnt3a signaling in the cell (IC100 at 10 µM) (data not shown). The compounds of Examples 1-6 also inhibited sclerostin inhibition of Wnt3a signaling and restored Wnt3a signaling in the cell.

Example 8: Bone Formation Assays

Mineralization (crystalline calcium phosphate formation) represents an in vitro model of bone formation. Using an assay in which the amount of mineralization is quantified by measuring total calcium after solubilization of deposited crystalline calcium phosphate, sclerostin was previously shown to inhibit mineralization in MC3T3-E1 (mouse calvarial) osteoblast cells. Li et al., J Bone Miner Res 24:578-588 (2008). Following the protocol described in Li et al., Compounds were assayed for their ability to rescue the inhibition of mineralization by sclerostin in MC3T3 osteoblast cells. Sclerostin treatment alone resulted in a significant decrease in mineralization, as measured by the calcium concentration (Table 1 and data not shown). Addition of a compound of Examples 1-6 neutralized sclerostin-mediated inhibition of mineralization, as reflected by the increase in calcium concentration.

Example 9: Metabolic Stability

Compounds of the present invention (0.1 µM) were incubated with microsomes at 37° C. for a total of 60 minutes. The reaction contained pooled human liver microsomal protein (0.1 mg/mL) in potassium phosphate buffer with NADPH. At the indicated time points (0, 5, 15, 30 and 60 minutes). Samples were analyzed by LC/MS/MS and remaining parent drug was calculated using Microsoft Excel (2007). Obach R S, *Drug Metab Dispos.* 27(11):1350-1359 (1999).

TABLE 1

Compound activity on modulating sclerostin/Wnt activity, sclerostin inhibition of mineralization, and metabolic stability.

| Example | Sclerostin Inhibition Assay; improvement over sclerostin alone | Sclerostin Inhibition of Mineralization; improvement over sclerostin alone | Metabolic Stability |
|---|---|---|---|
| Sclerostin protein | − | − | − |
| 1 | + | + | ++ |
| 2 | − | − | ++ |
| 3 | ++ | ++ | ++ |
| 4 | ++ | ++ | ++ |
| 5 | ++ | ++ | ++ |
| 6 | ++ | ++ | ++ |

− indicates no improvement over sclerostin protein alone
+ indicates an IC100 >10 µM
++ indicates an IC100 <10 µM
+ indicates a stability of <1x
++ indicates a stability >1x Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A pharmaceutical composition comprising a compound selected from the group consisting of

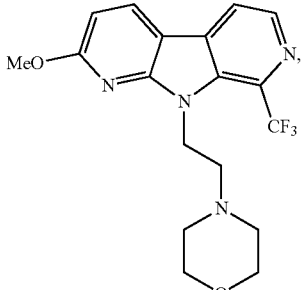

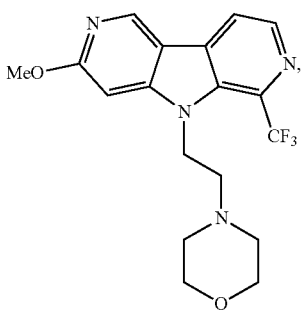

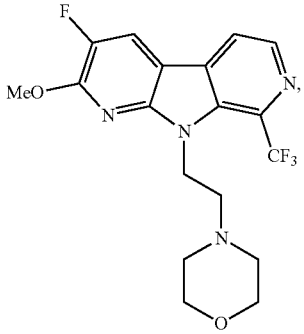

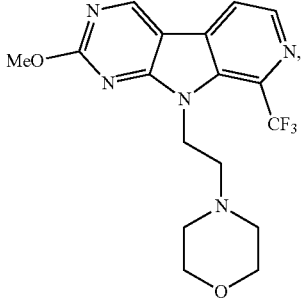

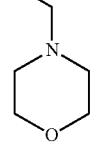 and

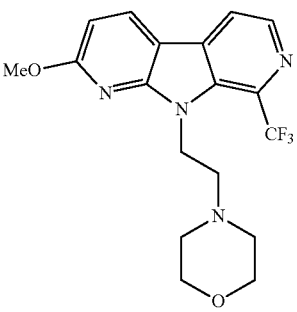 [SMILES: COc1ccc2c3ccnc(C(F)(F)F)c3n(CCN3CCOCC3)c2n1]

or a pharmaceutically acceptable salt thereof, and a pharmaceutically acceptable excipient or an osteoconductive matrix.

2. The pharmaceutical composition of claim 1, wherein the compounds has the formula

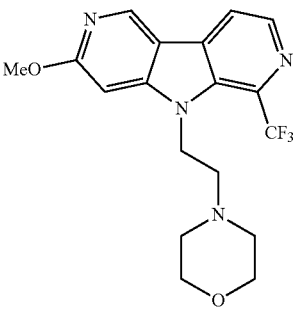

or a pharmaceutically acceptable salt thereof.

3. The pharmaceutical composition of claim 1, wherein the compounds has the formula

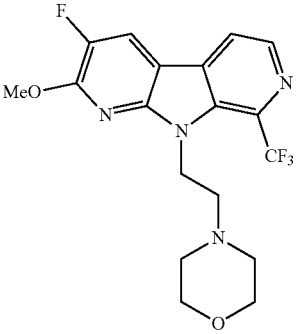 [SMILES: COc1nc2c(cc1F)c1ccnc(C(F)(F)F)c1n2CCN1CCOCC1]

or a pharmaceutically acceptable salt thereof.

4. The pharmaceutical composition of claim 1, wherein the compounds has the formula

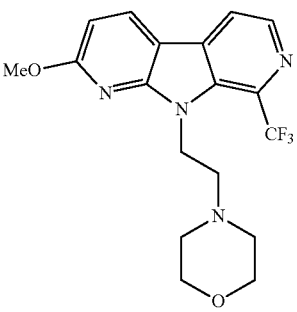 [SMILES: COc1ccc2c3ccnc(C(F)(F)F)c3n(CCN3CCOCC3)c2n1]

or a pharmaceutically acceptable salt thereof.

5. The pharmaceutical composition of claim 1, wherein the compounds has the formula

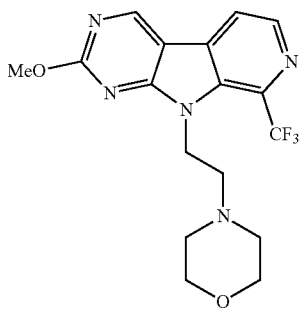 [SMILES: COc1ncc2c3ccnc(C(F)(F)F)c3n(CCN3CCOCC3)c2n1]

or a pharmaceutically acceptable salt thereof.

6. The pharmaceutical composition of claim 1, wherein the compounds has the formula

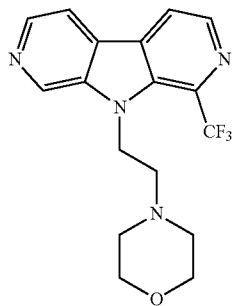 [SMILES: FC(F)(F)c1nccc2c3ccncc3n(CCN3CCOCC3)c12]

or a pharmaceutically acceptable salt thereof.

7. The pharmaceutical composition of claim 1, wherein the compounds has the formula

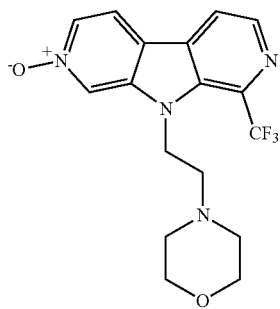

or a pharmaceutically acceptable salt thereof.

8. The pharmaceutical composition of claim 1, comprising an osteoconductive matrix.

9. The pharmaceutical composition of claim 8, wherein the osteoconductive matrix comprises an osteoinductive agent selected from the group consisting of bone allograft, bone autograft, and periodontal ligament cells.

10. The pharmaceutical composition of claim 8, wherein the osteoconductive matrix comprises a calcium salt, calcium sulfate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a biocompatible ceramic, a calcium phosphate ceramic, demineralized bone matrix, biphasic calcium phosphate, biocomposite, tantalum, titanium, polytetrafluoroethylene, sulfate salt, hydrogel, bioglass, or combinations thereof.

11. The pharmaceutical composition of claim 8, further comprising an antiresorptive drug.

12. The pharmaceutical composition of claim 11, wherein the antiresorptive drug is selected from the group consisting of denosumab, prolia, a RankL inhibitor, a bisphosphonate, a selective estrogen receptor modulator (SERM), calcitonin, a calcitonin analog, Vitamin D, a Vitamin D analog, and a cathepsin K inhibitor.

13. The pharmaceutical composition of claim 11, wherein the antiresorptive drug is denosumab.

14. The pharmaceutical composition of claim 8, further comprising an anabolic agent.

15. The pharmaceutical composition of claim 14, wherein the anabolic agent is selected from the group consisting of a parathyroid hormone (PTH) or an analog thereof, sclerostin inhibitors, bone morphogenic protein (BMP), a BMP agonist, a population of bone marrow stem cells, and a population of mesenchymal stem cells.

16. The pharmaceutical composition of claim 15, wherein the anabolic agent is a parathyroid hormone (PTH) or an analog thereof.

17. The pharmaceutical composition of claim 15, wherein the anabolic agent is a BMP selected from the group consisting of BMP2, BMP7 and BMP4.

18. A compound selected from the group consisting of

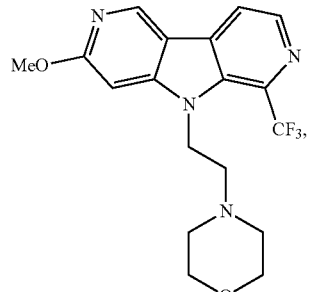

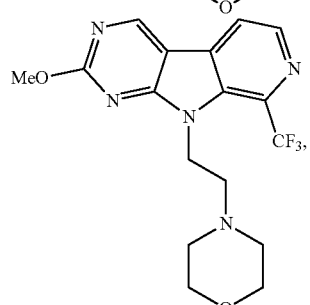

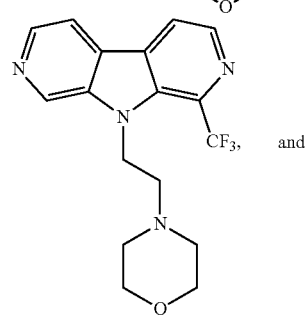

and

-continued

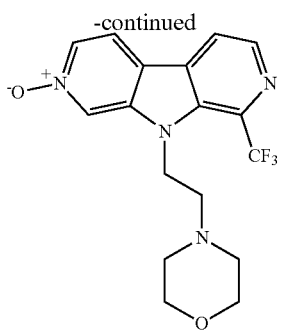

or a pharmaceutically acceptable salt thereof.

19. The compound of claim 18, having the formula

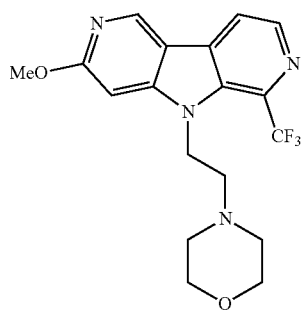

or a pharmaceutically acceptable salt thereof.

20. The compound of claim 18, having the formula

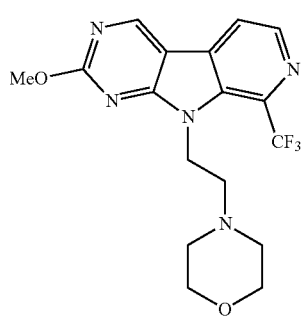 [SMILES: COc1ncc2c3ccnc(C(F)(F)F)c3n(CCN3CCOCC3)c2n1]

or a pharmaceutically acceptable salt thereof.

21. The compound of claim 18, having the formula

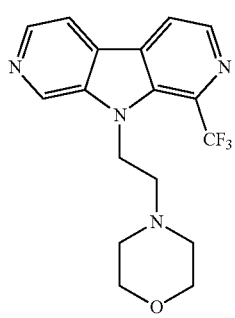 [SMILES: FC(F)(F)c1nccc2c3ccncc3n(CCN3CCOCC3)c12]

or a pharmaceutically acceptable salt thereof.

22. The compound of claim 18, having the formula

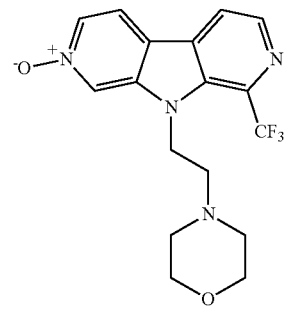

or a pharmaceutically acceptable salt thereof.

23. A method of promoting bone formation in a subject in need thereof, comprising administering to the subject a therapeutically effective amount of a compound selected from the group consisting of

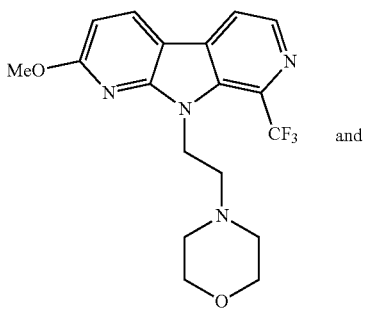

and

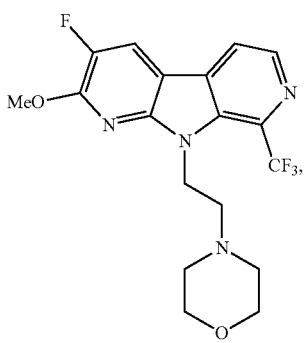

or a pharmaceutically acceptable salt thereof.

* * * * *